(12) United States Patent
Hirth et al.

(10) Patent No.: US 6,410,533 B1
(45) Date of Patent: Jun. 25, 2002

(54) ANTIBACTERIAL COMPOUNDS

(75) Inventors: Bradford H. Hirth, Littleton; Andrew Janjigian, Cambridge; Fred Vinick, Lexington, all of MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 09/502,101

(22) Filed: Feb. 10, 2000

(51) Int. Cl.[7] ............... A61K 31/4439; A61K 31/5355; C07D 231/08; C07D 401/04
(52) U.S. Cl. ............... 514/235.8; 514/254.05; 514/341; 514/380; 544/140; 544/371; 546/211; 546/274.1; 546/275.4; 548/364.7; 548/370.4; 548/372.5
(58) Field of Search .................. 514/235.8, 254.05, 514/341, 380; 544/140, 371; 546/275.4, 211, 274.1; 548/364.7, 370.4, 372.5

(56) References Cited

U.S. PATENT DOCUMENTS

| | | | | |
|---|---|---|---|---|
| 2,933,391 A | * | 4/1960 | Feniak et al. | |
| 3,441,563 A | * | 4/1969 | Weissel et al. | |
| 3,753,395 A | * | 8/1973 | Poot et al. | |
| 4,808,210 A | * | 2/1989 | Tessier et al. | |
| 4,909,827 A | * | 3/1990 | Gebring et al. | |
| 5,174,808 A | * | 12/1992 | Wroblowsky et al. | |

FOREIGN PATENT DOCUMENTS

GB          1173214          * 12/1969

OTHER PUBLICATIONS

"Results from Library Synthesis and Screening: a Biotech. Case Study," published in the book of Abstracts from the Conference Exploiting Moloecular Diversity in San Diego, CA, Feb. 1–3, 1999.

* cited by examiner

*Primary Examiner*—T. A. Soloau
(74) *Attorney, Agent, or Firm*—Hamilton, Brook, Smith & Reynolds, P.C.

(57) ABSTRACT

The present invention provides compounds having useful antibacterial activity and pharmaceutical compositions comprising one or more of these compounds. The invention further relates to a method of treating a bacterial infection in a patient, comprising administering to the patient an effective mount of one or more of the antibacterial compounds of the invention.

23 Claims, No Drawings

ANTIBACTERIAL COMPOUNDS

BACKGROUND OF THE INVENTION

The development of antimicrobial chemotherapeutic agents has significantly reduced the morbidity and mortality associated with bacterial infections over the last century, particularly in developed countries. However, the emergence of drug-resistant bacterial strains threatens the resurgence of diseases long thought to have been conquered. For example, a growing number of cases of drug-resistant tuberculosis have been reported since the mid-1980s, and a recent increase in multiple drug resistant *Staphylococcus aureus* infections has been observed. As the prevalence of drug-resistant bacteria increases, there is a growing need for new antibacterial agents which are suitable for use against a variety of bacterial targets.

SUMMARY OF THE INVENTION

The present invention relates to compounds which are useful as antimicrobial agents, and, in particular, as antibacterial agents.

In one embodiment, the invention provides compounds of Formula I,

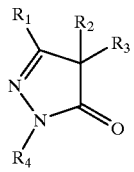

(I)

where $R_1$ is substituted or unsubstituted aryl, substituted or unsubstituted arylalkyl, substituted or unsubstituted alkyl, perfluoroalkyl, heteroaryl, carboxy, substituted or unsubstituted carboxamido, substituted or unsubstituted amino or alkoxycarbonyl. $R_2$ and $R_3$ are, independnetly, hydrogen; substituted or unsubstituted, linear, cyclic or branched alkyl; substituted or unsubstituted aminoalkyl; substituted or unsubstituted arylalkyl; substituted or unsubstituted heteroarylalkyl; or substituted or unsubstituted heteroarylcarbonyl and $R_3$ is hydrogen. $R_2$ and $R_3$ can also together form =N—OH or a substituted or unsubstituted alkylidene group. $R_1$ and $R_2$ can also together form —$(CH_2)_m$—, where m is 3 or 4. $R_4$ is a substituted or unsubstituted phenyl group.

In another embodiment, the compounds of the invention are of Formula II,

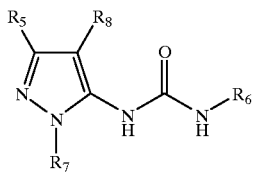

(II)

where $R_5$ is hydrogen; substituted or unsubstituted aryl; substituted or unsubstituted heteroaryl; substituted or unsubstituted arylalkyl; substituted or unsubstituted heteroarylalkyl; substituted or unsubstituted alkyl; carboxy; alkoxycarbonyl; substituted or unsubstituted aminoalkyl; or substituted or unsubstituted heterocycloalkyl-alkyl. $R_6$ is substituted or unsubstituted phenyl; $R_7$ is substituted or unsubstituted phenyl, substituted or unsubstituted alkyl or fluoroalkyl; and $R_8$ is halogen, phenyl, hydrogen or alkoxycarbonyl. $R_5$ and $R_8$ can also together form a substituted or unsubstituted alkylene group.

In yet another embodiment, the compounds of the invention are of Formula III,

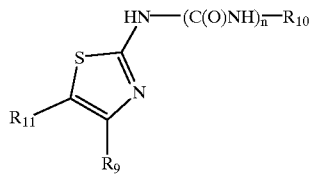

(III)

where n is 0 or 1. $R_9$ is hydrogen; substituted or unsubstituted aryl; substituted or unsubstituted heteroaryl; substituted or unsubstituted linear, branched or cyclic alkyl, alkoxy, alkoxycarbonyl, alkenyl or alkoxycarbonylcarbonyl; substituted or unsubstituted heterocycloalkyl; substituted or unsubstituted arylalkyl; substituted or unsubstituted heteroarylalkyl; substituted or unsubstituted heterocycloalkylalkyl. $R_{10}$ is substituted or unsubstituted aryl; substituted or unsubstituted heteroaryl; substituted or unsubstituted arylalkyl; or substituted or unsubstituted heteroarylalkyl; and $R_{11}$ is hydrogen, alkyl or alkylcarbonyl. $R_9$ and $R_{11}$ can also together form a substituted or unsubstituted alkylene group.

The invention also includes pharmaceutically acceptable salts of the compounds of Formulas I, II and III, and pharmaceutical compositions comprising one or more of these compounds and/or the salts thereof.

In another embodiment, the invention provides a method for treating a microbial infection in a patient. The method comprises administering to the patient a therapeutically effective amount of one or more compounds of Formula I, II or III.

DETAILED DESCRIPTION OF THE INVENTION

The present invention relates to antimicrobial compounds and salts thereof, pharmaceutical compositions comprising these compounds and methods of use thereof.

For the purposes of the present invention, the term "alkyl" refers to a straight chain or branched saturated hydrocarbyl group. Preferred alkyl groups include $C_1$–$C_{12}$-alkyl groups, while more preferred alkyl groups include $C_1$–$C_6$-alkyl groups. The term "cycloalkyl" refers to a mono-, bi- or polycyclic alkyl group. Preferred cycloalkyl groups include $C_3$–$C_8$-cycloalkyl groups. The term "alkoxy" refers to an alkyl-O— group or a cycloalkyl-O— group, where the preferred alkyl and cycloalkyl groups are those given above. The term "alkenyl" refers to a straight chain or branched hydrocarbyl group which includes one or more double bonds. Preferred alkenyl groups include $C_2$–$C_{12}$-alkenyl groups. The term "cycloalkenyl" refers to a cyclic hydrocarbyl group which includes one or more double bonds but is not aromatic. Preferred cycloalkenyl groups include $C_5$–$C_8$-cycloalkenyl groups.

The term "aryl" refers to an aromatic carbocyclic group, such as a phenyl group, a naphthyl group or a phenyl or naphthyl group which is fused with a a five or six-membered carbocyclic or heterocyclic ring.

The terms "heterocycle" and "heterocyclic group" refer to a saturated, aromatic or partially unsaturated ring system which includes at least one heteroatom, such as one or more oxygen, nitrogen or sulfur atoms or a combination thereof.

Saturated heterocyclic groups ("heterocycloalkyl groups") include piperidyl, pyrollidyl, piperazyl tetrahydrofuranyl and morpholyl.

The term "heteroaryl" refers to an aromatic heterocyclic group. Suitable heteroaryl groups include, but are not limited to, pyridyl, pyrimidyl, quinolyl, isoquinolyl, pyrrolyl, quinoxalyl, imidazolyl, oxazolyl, isoxazolyl, pyrazolyl, thienyl, furanyl, pyrazolyl, thiadiazolyl, oxadiazolyl, indazolyl, thiazolyl, isothiazolyl, and tetrazolyl. Heteroaryl groups also include ring systems in which a carbocyclic aromatic ring, carbocyclic non-aromatic ring or heteroaryl ring is fused to one or more other heteroaryl rings (e.g., benzo(b)thienyl, benzimidazolyl, benzoxazolyl, benzothiazolyl, benzothiadiazolyl, benzoxadiazolyl, indolyl, tetrahydroindolyl, azaindolyl, indazolyl, quinolinyl, imidazopyridyl, puryl, pyrrolo[2,3-d]pyrimidyl, pyrazolo[3,4-d]pyrimidyl).

The term "arylalkyl" refers to an alkyl group which is substituted by one or more substituted or unsubstituted aryl groups. Preferred arylalkyl groups include benzyl, diphenylmethyl and 2-phenethyl groups. The term "heteroarylalkyl" refers to an alkyl group which is substituted by a substituted or unsubstituted heteroaryl group.

Alkyl, cycloalkyl, alkenyl, cycloalkenyl and alkoxy groups can be substituted or unsubstituted. Substituted groups of this type can include, for example, one or more substituents such as halo, including fluoro, chloro, bromo and iodo; alkyl, such as $C_1$–$C_6$-alkyl; nitro; cyano; aryl groups, cycloalkyl groups and heterocyclic groups.

Aryl and heterocyclic, such as heteroaryl, groups can be substituted or unsubstituted. Suitable substituents include one or more substituents independently selected from halo, such as fluoro, chloro, bromo or iodo; alkyl, preferably $C_1$–$C_3$-alkyl; alkoxy, preferably $C_1$–$C_3$-alkoxy; nitro; methylenedioxo; aryl groups and heterocyclic groups.

In one embodiment, the invention provides compounds of Formula I,

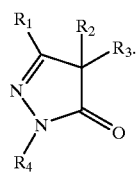

(I)

In one embodiment, $R_1$ is selected from the group consisting of carboxy, substituted and unsubstituted amino, substituted and unsubstituted phenyl; substituted and unsubstituted benzyl; linear and branched $C_1$–$C_6$-alkyl; trifluoromethyl; and substituted and unsubstituted pyridyl. For example, suitable identities for $R_1$ include phenyl, 4-methylphenyl, 2-methylphenyl, 3-methylphenyl, 4-fluorophenyl, 3-fluorophenyl, 2-fluorophenyl, methyl, trifluoromethyl, ethyl, n-propyl, 2-propyl, n-pentyl, 2-pentyl, 3-pentyl, 4-(1-morpholinyl)phenyl, 4-(4-carboxy-1-piperazinyl)phenyl; 2-pyridylcarbonyl; amino, carboxy and benzyl.

$R_2$ and $R_3$ are preferably selected from the group consisting of hydrogen, dimethylaminomethyl, methyl, ethyl, 2-propyl, 1-pyrrolidinyl-$C_1$–$C_4$-alkyl; pyridyl-$C_1$–$C_4$-alkyl; 3-carboxyphenylmethyl, 4-carboxyphenylmethyl, 3-(1-morpholinylcarbonyl)phenylmethyl. In one embodiment, $R_3$ is hydrogen and $R_2$ is selected from among the foregoing groups.

In another embodiment, $R_2$ and $R_3$ together form an alkylidene group or =N—OH. For example, the alkylidene group can be a substituted or unsubstituted linear or branched $C_1$–$C_6$-alkylidene group. Suitable substituents include amine, hydroxy, carboxy, substituted or unsubstituted aryl and substituted or unsubstituted hetercyclic groups. In one embodiment the substituent is substituted or unsubstituted phenyl or a substituted or unsubstituted heteroaryl group, such as a pyrrolyl, pyridyl, thienyl, indolyl, furanyl or thiazolyl group. The substituent can also be a substituted or unsubstituted heterocyclic group, such as a piperidinyl, indolinyl, morpholyl, pyranyl or thiopyranyl group. Suitable alkylidene groups include, but are not limited to, 4-methoxyphenyl-CH=; dimethylamino-CH=; 2-,3- or 4-pyridyl-CH=; isopropylidene; 2-,3- or 4-carboxyphenyl-CH=; methycarbonyl-CH=; phenylcarbonyl-CH=; 4-(N,N-diethylamino)phenyl-CH=; 4-(3-(N,N-dimethylamino)propoxy)phenyl-CH=; 2-,3- or 4-pyridyl-CH=; 1-methyl-4-piperidinyl-CH=; N-methyl-2-pyrrolyl-CH=; 2- or 3-thienyl-CH=; 2- or 3-furanyl-CH=; 2-thiazolyl; 4-thiomethoxyphenyl-CH=; 2- or 3-indolyl CH=; 4-thiopyranyl-CH=; 1-(N-ethoxycarbonyl)-4-piperidinyl-CH=; 3-(2-oxo)indolyl-CH=; N-methyl-3-indolyl-CH=; 2-,3- or 4-methoxycarbonylphenyl-CH=; 2-hydroxymethylfuranyl-CH=; $(HO_2C)CH=$; $(HO_2C)_2CH=$; $HO_2CCH_2CH=$; 3-(2-oxo indolinyl)-CH=; 3-(4-methylpiperidinylcarbonyl) phenyl-CH=; 3-(morpholyl-4-carbonyl)phenyl-CH= and 3-(N-(2-hydroxyethyl)aminocarbonylphenylCH=.

$R_1$ and $R_2$ can also together form an alkylene group, such as —$(CH_2)_3$— or —$(CH_2)_4$—.

$R_4$ is, preferably, a phenyl group substituted by one or more halo, trifluoromethyl, nitro or cyano groups, preferably chloro or trifluoromethyl. Suitable examples of such groups include, but are not limited to, 3,5-dichlorophenyl and 3,5-bis(trifuoromethyl)phenyl.

In another embodiment, the invention relates to compounds of Formula II,

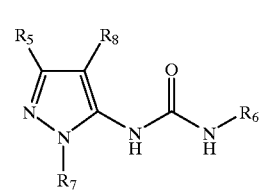

(II)

In one embodiment, $R_5$ is substituted or unsubstituted phenyl; substituted or unsubstituted pyridyl; substituted or unsubstituted thienyl; substituted or unsubstituted furyl; substituted or unsubstituted isoxazolyl, substituted or unsubstituted linear or branched $C_1$–$C_6$-alkyl; substituted or unsubstituted di-$C_1$–$C_6$-alkylaminomethyl or $C_1$–$C_6$-alkoxycarbonyl. In a preferred embodiment, $R_5$ is selected from the group consisting of phenyl, tert-butyl, 2-thienyl, 3-pyridyl, 2-pyridyl, 4-pyridyl, benzyl, 4-(1-morpholyl) phenyl, dimethylaminomethyl, 1-morpholylmethyl, 2-furyl, 5-methyl-3-isoxazolyl, 3-furyl, 3-thienyl, bis(2-methoxyethyl)aminomethyl, methyl, bis(2-hydroxyethyl) aminomethyl, ethoxycarbonyl, carboxy and hydroxymethyl.

$R_6$ is, preferably, a substituted or unsubstituted phenyl group, for example, a phenyl group which has one or more substituents independently selected from halogen, such as chloro, nitro, cyano and fluoroalkyl, preferably trifluoromethyl. Suitable identities for $R_6$ include, but are not limited to, 4-chloro-3-trifluoromethylphenyl, 3,5-bis (trifluoromethyl)phenyl and 3,5-dichlorophenyl.

$R_7$ is, preferably, a substituted or unsubstituted phenyl, substituted or unsubstituted linear or branched $C_1$–$C_6$-alkyl group or a linear or branched $C_1$–$C_6$-fluoroalkyl group. For example, suitable identities for $R_7$ include phenyl groups having one or more substituents independently selected from halogen, such as fluoro, bromo and chloro, and $C_1$–$C_6$-fluoroalkyl groups, preferably trifluoromethyl. In one embodiment, $R_7$ is selected from the group consisting of 4-trifluoromethylphenyl, 4-bromophenyl, 4-chlorophenyl and 2,2,2-trifluoroethyl.

$R_8$ is hydrogen, halogen, substituted or unsubstituted phenyl or alkoxycarbonyl, such as linear or branched $C_1$–$C_6$-alkoxycarbonyl. In preferred embodiments, $R_8$ is selected from the group consisting of hydrogen, phenyl, chloro, bromo, methoxycarbonyl and ethoxycarbonyl.

In a further embodiment, the present invention relates to compounds of Formula III,

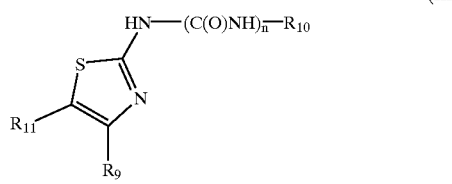

(III)

wherein n is 0 or 1. In one embodiment, $R_9$ is substituted or unsubstituted phenyl; substituted or unsubstituted arylalkyl; substituted or unsubstituted isoxazolyl; substituted or unsubstituted naphthyl; substituted or unsubstituted thienyl; substituted or unsubstituted linear, branched or cyclic $C_1$–$C_6$-alkyl, substituted or unsubstituted $C_1$–$C_6$-alkoxycarbonyl, substituted or unsubstituted $C_1$–$C_6$-alkoxycarbonylcarbonyl; $C_3$–$C_8$-cycloalkyl or $C_2$–$C_6$-alkenyl. Suitable substituents on the alkyl, cycloalkyl, alkoxycarbonyl and alkenyl groups include halogen atoms, carboxy groups and hydroxyl groups. $R_9$ can be also be phenyl, phenylalkyl, where the phenyl group is optionally substituted with one or more substituents independently selected from the group consisting of fluoro, chloro, bromo, methyl, trifluoromethyl, methoxy, difluoromethoxy, phenyl and 2-hydroxyethyl. Preferred identities for $R_9$ include phenyl, p-tolyl, 4-chlorophenyl, 4-trifluoromethylphenyl, 4-fluorophenyl, 4-methoxyphenyl, 4-cyanophenyl, 4-hydroxymethylphenyl, 4-(2-hydroxyethyl)phenyl, 2,4-dichlorophenyl, 2,4-difluorophenyl, 3,4-dichlorophenyl, 3,4-difluorophenyl, 4-fluoro-3-methylphenyl, 2-naphthyl, 4-bromophenyl, 3-fluorophenyl, 3,4-difluorophenyl, 4-difluoromethoxyphenyl, 3-ethoxycarbonyl-4-isoxazolyl, 3-ethoxycarbonyl-5-isoxazolyl, 3-carboxy-5-isoxazolyl, 3-hydroxymethyl-5-isoxazolyl, 3-phenyl-4-furyl, n-butyl, cyclopentyl, carboxymethyl, 2,5-dimethoxyphenyl, 2-naphthyl, 2-(2-dioxolanyl)ethyl, 2-thienyl, ethoxycarbonyl, 3-fluorophenyl, 2-methoxyphenyl, 3-methoxyphenyl, 4-phenylphenyl, 3,6-dimethylbenzo[b]-2-thienyl, 4-bromophenyl, methyl, t-butyl, but-3-enyl, ethoxycarbonyl, ethoxycarbonylcarbonyl; propoxycarbonyl and 3-hydroxypropyl.

In one embodiment, $R_{10}$ is substituted or unsubstituted phenyl, substituted or unsubstituted benzyl, or substituted or unsubstituted, linear, branched or cyclic $C_1$–$C_6$-alkyl. For example, $R_{10}$ can be phenyl or benzyl; or phenyl or benzyl substituted with one or more substituents independently selected from the group consisting of chloro, bromo, trifluoromethyl, trifluoromethoxy, methoxy, methylcarbonyl, t-butyl and difluoromethoxy. Preferably, $R_{10}$ is selected from the group consisting of 3-bromophenyl, 3-trifluoromethoxyphenyl, 3,5-bis(trifluoromethyl)phenyl, 2,4,5-trichlorophenyl, 4-fluoro-3-trifluoromethylphenyl, 3-thiomethoxyphenyl, 4-difluoromethoxyphenyl, 2-fluoro-3-trifluoromethylphenyl, 4-trifluoromethylthiophenyl, 3,4,5-trimethoxyphenyl, 4-methylcarbonylphenyl, 3,5-di-t-butylphenyl, 3,4-dichlorophenylmethyl, 3-chlorophenylmethyl, methyl-3-chlorophenylmethyl, 2-methoxyphenylmethyl, 2-bromophenylmethyl, 3-bromophenylmethyl, 3-fluorophenylmethyl, and 3-phenyl-3-hydroxy-2-propyl.

$R_{11}$ is selected from the group consisting of hydrogen, alkyl, alkoxycarbonyl and alkylcarbonyl. For example, $R_{11}$ can be, but is not limited to, methyl, methylcarbonyl, methoxycarbonyl and ethoxycarbonyl.

$R_9$ and $R_{11}$ can also form together substituted or usubstituted alkylene group, or an alkylene group interrupted at one or more points by a heteroatom, such as an oxygen, nitrogen or sulfur atom. For example, $R_9$ and $R_{11}$ can together form a group such as —$(CH_2)_n$—, where n is 3, 4 or 5; 2,2-ethylenedioxobutylene (—$CH_2C(O(CH_2)_2O)CH_2CH_2$—).

The present invention further relates to pharmaceutically acceptable salts of the compounds of Formulas I, II and III. A "pharmaceutically acceptable salt" is a salt which retains the biological effectiveness and properties of the free base and which can be obtained by reaction with an inorganic or organic acid, such as hydrochloric acid, hydrobromic acid, sulfuric acid, nitric acid, phosphoric acid, organic sulfonic acid, organic carboxylic acid, organic phosphoric acid, for example, methanesulfonic acid, ethanesulfonic acid, p-toluenesulfonic acid, salicylic acid, lactic acid, tartaric acid and the like.

In another embodiment, the present invention relates to a method of treating a microbial infection in a patient. The method comprises the step of administering to the patient a therapeutically effective amount of one or more compounds of Formulas I, II or III, as described above. The patient to be treated can be any animal, and is preferably a mammal, such as a domesticated animal or a livestock animal. More preferably, the patient is a human.

The microbial infection is, preferably, an infection by a bacterial species, and is, generally, an infection by a pathogenic bacterial species. Microbial infections which can be treated using the compounds of the invention include infections by one or more pathogenic bacterial species. Examples of pathogenic bacterial species which cause infections which can be treated using the compounds of the invention include Mycobacterium species, such as *M. tuberculosis, M. avian-intracellulare, M. kansasii, M. bovis, M. africanum, M. genavense, M. leprae, M. xenopi, M. simiae, M. scrofulaceum, M. malmoense, M. celatum, M. abscessus, M. chelonae, M. szulgai, M. gordonae, M. haemophilum, M. fortuni* and *M. marinum;* Staphylococcus species, such as *S. aureus;* Streptococcus species, such as *S. pyogenes* and *S. pneumoniae;* Enterococcus species, such as *E. faecalis;* Corynebacterium species, such as *C. diphtheriae;* Vibrio species, such as *V. cholerae;* Campylobacter species, such as *C. jejuni;* Helicobacter species, such as *H. pylori;* Pseudomonas species, such as *P. aeruginosa;* Haemophilus species, such as *H. influenzae;* Legionella species, such as *L. pneumophila;* Treponema species, such as *T. pallidum;* Borrelia species, such as *B. burgdorferi;* Listeria species, such as *L. monocytogenes;* Bacillus species, such as *B. cereus;* Bordatella species, such as *B. pertussis;* Clostridium species, such as *C. perfringens, C. tetani, C. difficile* and *C. botulinum;* Neisseria species, such as *N. meningitidis* and *N. gonorrhoeae;* Chlamydia species, such as *C. psittaci, C. pneumoniae* and *C. trachomatis;* Rickettsia species, such as *R. rickettsii* and *R. prowazekii;* Shigella species, such as *S.*

*sonnei;* Salmonella species, such as *S. typhimurium;* Yersinia species, such as *Y. enterocolitica* and *Y. pseudotuberculosis;* Klebsiella species, such as *K. pneumoniae;* Escherichia species, such as *E. coli,* including enterotoxigenic, enteropathogenic, enteroinvasive, enterohemorhagic and enteroaggregative *E. coli* strains.

In one embodiment, the microbial infection is an infection by *S. aureus* or *S. pneumoniae.*

The compounds of the invention can also be used prophylactically. That is, a compound or set of compounds of Formula I, II or III can be administered to an individual deemed to be at risk for developing a microbial infection. Individuals at risk for developing a microbial infection include individuals who have been exposed to a particular microorganism, such as a pathogenic bacterial species; individuals having a compromised immune system, such as individuals suffering from an immunodeficiency disease or taking immunocompromising medication; and individuals having a history of repeated or chronic infection, such as children who have repeated infections of the middle ear.

A "therapeutically effective amount" is an amount of a compound of Formula I, II or III, or a combination of two or more such compounds, which inhibits, totally or partially, the progression of the microbial infection or alleviates, at least partially, one or more symptoms of the microbial infection. A therapeutically effective amount can also be an amount which is prophylactically effective, that is, an amount which is effective to prevent the development of a microbial infection. The amount which is therapeutically effective will depend upon the patient's size and gender, the condition to be treated, the severity of the condition and the result sought. For a given patient, a therapeutically effective amount can be determined by methods known to those of skill in the art.

The compound or compounds of Formulas I, II or III can be administered alone or in combination with one or more additional therapeutic agents, as can be selected by one of skill in the art. For example, the compound or compounds of the invention can be administered in combination with one or more antimicrobial agents, such as those known in the art. For example, one or more compounds of Formulas I, II or III can be administered in combination with one or more agents, such as antimicrobial agents, which can be employed in the treatment of the particular microbial infection. Suitable antimicrobial agents are known in the art and include isoniazid, rifampin, pyrazinamide, ethambutol, erythromycin, vancomycin, tetracycline, chloramphenicol, ampicillin, chephalosporins, sulfonamides, gentamicin, amoxicillin, penicillin, streptomycin, p-aminosalicyclic acid, clarithromycin, clofazimine, minocycline, sulfonamides, ethionamide, cycloserine, kanamycin, amikacin, capreomycin, viomycin, thiacetazone, rifabutin and the quinolones, such as ciprofloxacin, ofloxacin and sparfloxicin.

If two or more compounds of the invention are administered in combination, they can be administered simultaneously, sequentially or separately, for example, with administration of each compound or two or more groups of compounds separated by a suitable time interval, such as hours. When the compound or compounds of the invention are administered in combination with one or more additional agents, such as are discussed above, the compound or compounds of the invention can be and the additional agents or agents can be administered simultaneously, sequentially or separately, for example, with administration of each agent or two or more groups of agents separated by a suitable time interval, such as hours.

The compounds of this invention can be administered to the patient by themselves or in pharmaceutical compositions in which they are mixed with one or more suitable carriers and/or excipients at doses sufficient to treat the microbial infection. Mixtures of these compounds can also be administered to the patient as a simple mixture or in suitable formulated pharmaceutical compositions. Techniques for formulation and administration of the compounds of the instant application are known in the art and can be found, for example, in "Remington: the Science and Practice of Pharmacy," 19$^{th}$ edition, Mack Publishing Co., Easton, Pa. (1995).

Suitable routes of administration can, for example, include oral, ocular (eyedrop), rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections. In one embodiment, the compound of the invention is administered to the skin.

Alternatively, one can administer the compound in a local rather than a systemic manner, for example, via injection of the compound directly into a site of localized infection, often in a depot or sustained release formulation.

Furthermore, one can administer the drug in a targeted drug delivery system, for example, in a liposome coated with an antibody which is selective for a particular tissue.

The pharmaceutical compositions of the present invention can be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus can be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention can be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include push-fit capsules made of a suitable material, such as gelatin, as well as soft, sealed capsules made of a suitable material, for example, gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit can be determined by providing a valve to deliver a metered amount. Capsules and cartridges of a suitable material, such as gelatin, for use in an inhaler or insufflator can be formulated containing a powder mix of the compound and a suitable powder base such as lactose or starch.

The compounds can be formulated for parenteral administration by injection, e.g. bolus injection or continuous infusion. Formulations for injection can be presented in unit dosage form, e.g. in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions.

Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example subcutaneously or intramuscularly or by intramuscular injection). Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in an effective amount to achieve the intended purpose. More specifically, a therapeutically effective amount means an amount effective to prevent development of or to alleviate the existing symptoms of the subject being treated. Determination of the effective amounts is well within the capability of those skilled in the art.

For any compound used in the method of the invention, the therapeutically effective dose can be estimated initially from in vitro assays and animal models. For example, a dose can be formulated in cellular and animal models to achieve a circulating concentration range that includes the $IC_{50}$ as determined in cellular assays (i.e., the concentration of the test compound which achieves a 50% reduction in bacterial growth). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit microbial growth at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition. (see, for example, Ross in "Goodman and Gilman's The Pharmacological Basis of Therapeutics", Gilman et al., ed. Chapter 2 (1990) and Benet et al. in "Goodman and Gilman's The Pharmacological Basis of Therapeutics", Gilman et al., ed. Chapter 1 (1990)). In the treatment of crises, the administration of an acute bolus or an infusion approaching the MTD may be required to obtain a rapid response.

Dosage amount and interval can be adjusted individually to provide plasma levels of the active moiety which are sufficient to maintain the desired effects, or minimal effective concentration (MEC). The MEC will vary for each compound but can be estimated from in vitro data; e.g. the concentration necessary to achieve 50–90% inhibition of bacterial growth using the assays described herein. Dosages necessary to achieve the MEC will depend on individual characteristics and route of administration. However, HPLC assays or bioassays can be used to determine plasma concentrations. Dosage intervals can also be determined using the MEC value. For example, compounds can be administered using a regimen which maintains a plasma level above the MEC for 10–90% of the time, preferably between 30–90% and most preferably between 50–90% until the desired amelioration of symptoms is achieved. In cases of local administration or selective uptake, the effective local concentration of the drug may not be related to plasma concentration.

The amount of composition administered will be dependent on the subject being treated, on the subject's weight, the severity of the affliction, the manner of administration and the judgment of the prescribing physician.

Compounds of Formulas I, II and III are also of use as antiseptic agents, for example, in soaps, such as hand soaps, hand scrubs and medical devices, such as catheters. When used as an antiseptic on the surface of a medical device, one or more compounds of Formulas I, II and III can be present in an antiseptic composition, which can, optionally, include one or more antiseptic agents or other agents, as are known in the art, which provide suitable consistency, stability or other chemical or physical properties appropriate for the intended method of use. For example, an antiseptic composition for the surface of a medical device can which includes one or more components which enable the composition to adhere to the surface of the device. In one embodiment, the compound or compounds of Formulas I, II or III is formulated with a polymeric material.

Compounds of Formulas I, II and III are also useful as antiseptics in wounds and can be applied directly to a wound to inhibit microbial infection of the wound. In one embodiment, the compound or compounds of Formulas I, II or III are present on and/or in a wound dressing, such as a bandage.

EXAMPLES

Example 1

2-(3,5-Dichloro-phenyl)-5-phenyl-2,4-dihydro-pyrazol-3-one (Compound 1)

A solution of ethyl benzoylacetate (0.192 g, 1.00 mmol), 3,5-dichlorophenylhydrazine hydrochloride (0.235 g, 1.10 mmol), and p-toluenesulfonic acid monohydrate (0.019 g, 0.10 mmol) in ethanol (10 mL) was heated at reflux for 24 hours. The reaction solution was concentrated and the resulting residue was partitioned between ethyl acetate and aqueous 1N hydrochloric acid solution. The organic layer was further washed with water and brine, dried (sodium sulfate) and concentrated to afford a yellow solid. The crude product was triturated with hexanes and collected by suction filtration. Air drying afforded 0.174 g (57%) of product as a bright yellow solid: $^1$H NMR (DMSO-$d_6$) δ12.60–12.40 (br s, 1H), 7.92 (s, 2H), 7.87–7.83 (d, 2H), 7.50 (s, 1H), 7.44–7.38 (m, 2H), 7.36–7.31 (m, 1H), 6.02 (s, 1H) ppm.

Example 2

2-(3,5-Dichloro-phenyl)-4-(4-methoxy-benzylidene)-5-phenyl-2,4-dihydro-pyrazol-3-one (Compound 3)

A solution of compound 1 (0.310 g, 1.02 mmol) and 4-methoxybenzaldehyde (0.140 g, 1.03 mmol) in acetic acid (10 mL) was heated at reflux for 24 hours. The reaction solution was concentrated and the resulting residue was triturated with hexanes and collected by suction filtration. Air drying afforded 0.080 g (19%) of product as a yellow solid: $^1$H NMR (DMSO-$d_6$) δ7.98–7.94 (d, 2H), 7.52 (s, 1H), 7.42–7.38 (m, 1H), 7.30–7.18 (m, 4H), 7.09–7.04 (d, 2H), 6.85–6.80 (d, 2H), 3.66 (s, 3H) ppm.

Example 3

2-(3,5-Dichloro-phenyl)-4-dimethylaminomethylene-5-phenyl-2,4-dihydro-pyrazol-3-one (Compound 9)

To a solution of compound 1 (0.305 g, 1.00 mmol) in N,N-dimethylformamide (10 mL) was added tert-butoxybis(dimethylamino)methane (0.349 g, 2.00 mmol). The reaction solution was stirred for 72 hours, then partitioned between brine and ethyl acetate. The organic layer was dried (magnesium sulfate) and concentrated to afford a brown oil. Trituration of the oil with hexanes produced a yellow solid which was filtered and air dried to yield 0.123 g (34%): $^1$H NMR (DMSO-$d_6$) δ8.14–8.10 (d, 2H), 7.61–7.53 (m, 3H), 7.51–7.42 (m, 3H), 7.32–7.28 (t, 3H), 3.33–3.28 (s, 6H) ppm.

Example 4

2-(3,5-Dichloro-phenyl)-5-phenyl-2H-pyrazole-3,4-dione-4-oxime (Compound 23)

A solution of compound 1 (0.305 g, 1.00 mmol) in acetic acid (50 mL) was cooled to 5° C. in an ice bath. Sodium nitrite (0.107 g, 1.47 mmol) in water (5 mL) was added dropwise over 10 minutes to above. The reaction was stirred for 1 hour at 5° C., allowed to come to room temperature and stirred for an additional 1 hour. The reaction solution was partitioned between water and ethyl acetate. The organic layer was further washed with water and brine, dried (magnesium sulfate) and concentrated to afford 0.270 g (80%) of product as a bright orange solid: $^1$H NMR (CDCl$_3$) δ14.30 (s, 1H), 8.25–8.20 (d, 2H), 8.02 (s, 2H), 7.61–7.45 (m, 3H), 7.38–7.22 (s, 1H) ppm.

Example 5

2-(3,5-Dichloro-phenyl)-4-(1-methyl-piperidin-4-ylidene)-5-phenyl-2,4-dihydropyrazol-3-one (Compound 31)

A solution of compound 1 (0.076 g, 0.25 mmol) and 1-methyl-4-piperidone (0.028 g, 0.25 mmol) in acetic acid (10 mL) was heated at reflux for 72 hours. The reaction solution was concentrated and the resulting residue was triturated with hexanes. Solid was collected by suction filtration. Air drying afforded 0.45 g (45%) of product as a bright yellow solid: $^1$H NMR (DMSO-$d_6$) δ8.32–8.20 (s, 2H), 7.51–7.38 (d, 2H), 7.38–7.15 (m, 3H), 7.01 (s, 1H), 5.49 (s, 1H), 3.60–3.45 (m, 4H), 3.24–3.04 (s, 3H), 2.68–2.62 (m, 4H) ppm.

Example 6

2-(3,5-Dichloro-phenyl)-5-phenyl-4-(pyridine-2-carbonyl)-2,4-dihydro-pyrazol-3-one (Compound 50)

To a solution of compound 1 (0.305 g, 1.00 mmol) in dioxane (7 mL) was added nicotinoyl chloride hydrochloride (0.196 g, 1.10 mmol), triethylamine (0.111 g, 1.10 mmol)

and calcium hydroxide (0.131 g, 3.11 mmol). The reaction was heated to reflux for 48 hours. The reaction solution was poured into a 1N aqueous hydrochloric acid solution. Solid precipitate was removed via filtration, washed with 2:1 hexanes/ethyl acetate and air dried to afford 0.157 g (38%) of product as an orange solid: $^1$H NMR (DMSO-$d_6$) δ14.30 (s, 1H), 8.25–8.20 (d, 2H), 8.02 (s, 2H), 7.61–7.45 (m, 3H), 7.38–7.22 (s, 1H) ppm.

Example 7

1-(3,5-Bis-trifluoromethyl-phenyl)-3-[5-phenyl-2-(4-trifluoromethyl-phenyl)-2H-pyrazol-3-yl]-urea (Compound 76)

Preparation of 5-Phenyl-2-(4-trifluoromethyl-phenyl)-2H-pyrazol-3-ylamine

A solution of benzoylacetonitrile (2.25 g, 15.5 mmol), 4-(trifluoromethyl)phenylhydrazine (3.00 g, 17.0 mmol) and triethylamine (4.3 mL, 31 mmol) in n-butanol (30 mL) was heated at reflux overnight. The reaction solution was concentrated and the resulting residue was partitioned between ethyl acetate and aqueous sodium bicarbonate solution. The organic layer was further washed with water and brine, dried over sodium sulfate and concentrated to afford a moist brown solid. The crude product was triturated with diethyl ether/hexane and collected by suction filtration. Air drying on the frit afforded 2.05 g (44%) of product as a tan solid: $^1$H NMR (DMSO-$d_6$) δ8.00–7.72 (m, 6H), 7.40–7.25 (m, 3H), 5.95 (s, 1H), 5.63 (s, 2H) ppm.

Preparation of Compound 76

To a stirred suspension of the product of step 1 (0.95 g, 3.1 mmol) in chloroform (12.5 mL) was added 3,5-bis(trifluoromethyl)phenyl isocyanate (0.57 mL, 3.3 mmol). After stirring the reaction overnight, solid was removed by suction filtration. The filtercake was rinsed with cold chloroform followed by hexane. Air drying on the frit afforded 1.54 g (88%) of compound 76 as a white solid: $^1$H NMR (DMSO-$d_6$) δ9.75 (s, 1H), 9.04 (s, 1H), 8.10 (s, 2H), 7.97–7.84 (m, 6H), 7.65 (s, 1H), 7.50–7.33 (m, 3H), 7.03 (s, 1H) ppm.

Example 8

1-(3,5-Bis-trifluoromethyl-phenyl)-3-[2-(4-bromo-phenyl)-5-pyridin-3-yl-2H-pyrazol-3-yl]-urea (Compound 117)

Preparation of Nicotinoylacetonitrile, Sodium Salt

To a stirred solution of ethyl nicotinate (2.31 g, 15.3 mmol) in tetrahydrofuran (25 mL) was added acetonitrile (0.80 mL, 15 mmol) and 60% mineral oil dispersion of sodium hydride (0.61 g, 15 mmol). The mixture was refluxed for 4 hours, cooled to room temperature and suction filtered to remove precipitate. The filtercake was rinsed with diethyl ether and vacuum oven dried to afford 2.13 g (90%) of the crude intermediate as a tan solid. The material was used without purification in the next reaction.

Preparation of 2-(4-Bromo-phenyl)-5-pyridin-3-yl-2H-pyrazol-3-ylamine

To a suspension of the product of step 1 (1.13 g, 7.33 mmol) in n-butanol (14 mL) was added 4-bromophenylhydrazine hydrochloride (1.72 g, 7.70 mmol). The reaction mixture was heated at reflux for 4 hours, cooled to room temperature and diluted with water (~100 mL) and methanol (~50 mL). The oil which separates was allowed to solidify and then agitated until forming a homogenous suspension. The light brown solid was collected by suction filtration and vacuum oven dried. Flash chromatography over silica (methylene chloride/methanol) afforded 1.26 g (55%) of the product as a tan solid: $^1$H NMR (CDCl$_3$) d 8.82 (s, 1H), 8.42–88.36 (m, 1H), 7.98–7.92 (m, 1H), 7.47 (d, J=8.9 Hz, 2H), 7.38 (d, J=8.9 Hz, 2H), 7.20–7.12 (m, 1H), 5.83 (s, 1H), 3.90 (s, 2H) ppm.

Preparation of Compound 117

Compound 117 was prepared from the product of step 2 using a procedure similar to that described in step 2 of the synthesis of compound 76. The title compound was afforded as an off-white solid: $^1$H NMR (DMSO-$d_6$) d 9.75 (s, 1H), 9.08 (s, 1H), 8.97 (s, 1H), 8.62–8.48 (m, 1H), 8.30–8.18 (m, 1H), 8.09 (s, 2H), 7.77 (d, J=8.2 Hz, 2H), 7.66 (s, 1H), 7.62 (d, J=8.2 Hz, 2H), 7.52–7.40 (m, 1H), 7.11 (s, 1H) ppm.

Example 9

1-(3,5-Bis-trifluoromethyl-phenyl)-3-[2-(4-bromo-phenyl)-5-methyl-2H-pyrazol-3-yl]-urea (Compound 95)

Preparation of (4-Bromo-phenyl)-5-methyl-2H-pyrazol-3-ylamine

A suspension of 3-aminocrotononitrile (3.60 g, 43.8 mmol) and 4-bromophenylhydrazine hydrochloride (9.81 g, 43.9 mmol) in 2:1 isopropanol/water (30 mL) was heated at reflux for 30 minutes. Concentrated hydrochloric acid (50 mL) was added and the mixture was refluxed for an additional 2 hours and then stirred overnight at room temperature. The reaction mixture was partitioned between ethyl acetate (~300 mL) and 1 N sodium hydroxide (~600 mL). The organic layer was combined with an additional ethyl acetate extract, dried over magnesium sulfate and concentrated to afford a dark amber oil. This material was taken up in a sufficient volume of hot hexane/ethyl acetate to achieve a homogenous solution. After overnight cooling, the resulting precipitate was removed by suction filtration and rinsed with hexane/ethyl acetate. Air drying on the frit afforded 6.29 g (57%) of product as a light brown, crystalline solid: $^1$H NMR (DMSO-$d_6$) d 7.59 (d, J=8.9 Hz, 2H), 7.51 (d, J=8.9 Hz, 2H), 5.32 (s, 1H), 5.30 (s, 2H), 2.02 (s, 3H) ppm.

Preparation of Compound 95

Compound 95 was prepared from the product of step 1 using a procedure similar to that described in step 2 of the synthesis of compound 76. The title compound was afforded as an off-white solid: $^1$H NMR (DMSO-$d_6$) 9.63 (s, 1H), 8.78 (s, 1H), 8.05 (s, 2H), 7.68 (d, J=8.7 Hz, 2H), 7.64 (s, 1H), 7.47 (d, J=8.2 Hz, 2H), 6.28 (s, 1H), 219 3H) ppm.

Example 10

1-(3,5-Bis-trifluoromethyl-phenyl)-3-[2-(4-bromo-phenyl)-2H-pyrazol-3-yl]-urea (Compound 92)

Preparation of 5-Amino-1-(4-bromo-phenyl)-1H-pyrazole-4-carboxylic acid ethyl ester A solution of 4-bromophenylhydrazine (2.76 g, 14.7 mmol) and ethyl (ethoxymethylene)cyanoacetate (2.50 g, 14.8 mmol) in ethanol (15 mL) was heated at reflux for 2 hours. Upon cooling, a tan precipitate formed. The suspension was diluted with diethyl ether and suction filtered to remove solid. The filtercake was rinsed with diethyl ether and vacuum oven dried to afford 3.20 g (70%) of product as a tan solid: $^1$H NMR (CDCl$_3$) d 7.79 (s, 1H), 7.64 (d, J=8.7 Hz, 2H), 7.45 (d, J=8.7 Hz, 2H), 5.30 (s, 2H), 4.31 (q, J=7.2 Hz, 2H), 1.37 (t, J=7.2 Hz, 3H) ppm.

Preparation of 5-Amino-1-(4-bromo-phenyl)-1H-pyrazole-4-carboxylic acid

A suspension of the product of step 1 (1.55 g, 5.00 mmol) in 1:1 methanol/2 N aqueous sodium hydroxide (20 mL) was heated at reflux for 1 hour. The reaction mixture was concentrated to dryness and the residue was taken up in water (30 mL). A small amount of undissolved solid was filtered away and the filtrate was neutralized by the addition of 1 N hydrochloric acid (20 mL). The resulting precipitate was collected by suction filtration, rinsed with water and vacuum oven dried to afford 1.34 g (95%) of product as an off-white solid: $^1$H NMR (DMSO-$d_6$) d 12.10 (s, 1H), 7.72 (d, J=8.6 Hz, 2H), 7.69 (s, 1H), 7.52 (d, J=8.6 Hz, 2H), 6.35 (s, 2H) ppm.

Preparation of 2-(4-Bromo-phenyl)-2H-pyrazol-3-ylamine

A neat sample of the product of step 2 (1.29 g, 4.57 mmol) was heated to its melting point (181–183° C.) in an oil bath. The frothy oil was maintained at this temperature for 10 minutes before cooling to room temperature. The resulting brown gum was filtered through a plug of silica (hexane/ethyl acetate) to afford 1.09 g (100%) of product as an amber solid: $^1$H NMR (CDCl$_3$) δ7.59 (d, J=8.6 Hz, 2H), 7.48 (d, J=8.6 Hz, 2H), 7.42 (s, 1H), 5.62 (s, 1H), 3.82 (s, 2H) ppm.

Preparation of Compound 92

Compound 92 was prepared from the product of step 3 using a procedure similar to that described in step 2 of the synthesis of compound 76. The title compound was afforded as a white solid: $^1$H NMR (DMSO-$d_6$) δ9.67 (s, 1H), 8.80 (s, 1H), 8.06 (s, 2H), 7.72 (d, J=8.7 Hz, 2H), 7.65 (s, 1H), 7.64 (s, 1H), 7.51 (d, J=8.2 Hz, 2H), 6.47 (s, 1H) ppm.

Example 11

1-(3,5-Bis-trifluoromethyl-phenyl)-3-[4-bromo-2-(4-bromo-phenyl)-2H-pyrazol-3-yl]-urea (Compound 97)

To a stirred suspension of compound 95 (0.200 g, 0.394 mmol) in carbon tetrachloride (5 mL) was added N-bromosuccinimide (0.074 g, 0.42 mmol) and benzoyl peroxide (0.005 g, 0.02 mmol). The mixture was heated at reflux for 2 hours, diluted with methylene chloride (~10 mL) and filtered to remove solid. The filtercake was rinsed with methylene chloride and vacuum oven dried to afford 0.208 g (90%) of product as a white solid: $^1$H NMR (DMSO-$d_6$) δ9.84 (s, 1H), 8.82 (s, 1H), 8.08 (s, 2H), 7.65 (d, J=8.8 Hz, 2H), 7.50 (s, 1H), 7.48 (d, J=8.8 Hz, 2H), 2.23 (s, 3H) ppm.

Example 12

1-(3,5-Bis-trifluoromethyl-phenyl)-3-[2-(4-bromo-phenyl)-5-hydroxymethyl-2H-pyrazol-3-yl]-urea (Compound 99)

To a stirred solution of compound 98 (1.79 g, 3.17 mmol) in tetrahydrofuran (50 mL) was added lithium borohydride (0.214 g, 9.83 mmol). The mixture was heated at reflux for 1.25 hours and then stirred at room temperature overnight. The reaction was quenched by the dropwise addition of dilute aqueous hydrochloric acid and concentrated. The resulting residue was partitioned between ethyl acetate and dilute aqueous hydrochloric acid. The organic layer was dried (magnesium sulfate) and concentrated to afford an off-white solid. Flash chromatography over silica (methylene chloride/methanol) afforded 1.33 g (80%) of product as a white solid: $^1$H NMR (DMSO-$d_6$) δ9.64 (s, 1H), 8.80 (s, 1H), 8.06 (s, 2H), 7.70 (d, J=8.9 Hz, 2H), 7.64 (s, 1H), 7.49 (d, J=8.9 Hz, 2H), 6.44 (s, 1H), 5.15 (t, J=7.5 Hz, 1H), 4.44 (d, J=7.5 Hz, 2H) ppm.

Example 13

1-(3,5-Bis-trifluoromethyl-phenyl)-3-[4-(4-chloro-phenyl)-thiazol-2-yl]-urea (Compound 138)

To a stirred solution of 2-amino-4-(4-chlorophenyl) thiazole (0.647 g, 3.07 mmol) in ethyl acetate (50 mL) was added 3,5-bis(trifluoromethyl)phenyl isocyanate (0.53 mL, 3.1 mmol). The mixture was refluxed for 16 hours, cooled to room temperature, and washed with 10% aqueous hydrochloric acid solution, water and brine. The mixture was dried (magnesium sulfate), filtered, and concentrated to provide a white solid. Flash chromatography over silica (hexanes/ethyl acetate) provided 0.850 g (59%) of the product as a white solid: $^1$H NMR (NMR (DMSO-$d_6$) δ9.62 (br s, 1H), 8.18–8.17 (m, 2H), 7.92–7.88 (m, 2H), 7.72–7.66 (m, 2H), 7.49–7.46 (m, 2H) ppm.

Example 14

1-[4-(4-Bromo-phenyl)-thiazol-2-yl]-3-(3-chloro-benzyl)-urea (Compound 175)

Preparation of [4-(4-Bromo-phenyl)-thiazol-2-yl]-carbamic acid phenyl ester

To a stirred solution of 2-amino-(4-bromophenyl)thiazole (2.16 g, 8.47 mmol) in tetrahydrofuran (70 mL) was added pyridine (0.89 mL, 11 mmol). The solution was cooled to 0° C. and treated with phenyl chloroformate (1.2 mL, 9.3 mmol). The thick white suspension was allowed to warm to room temperature and was stirred for 14 hours. The mixture was diluted with ethyl acetate (100 mL) and washed with 10% aqueous hydrochloric acid solution, water, and brine. The mixture was dried (magnesium sulfate), filtered, and concentrated to provide a yellow solid. Trituration of the crude solid with cold dichloromethane provided 2.11 g (66%) of the product as a white solid: $^1$H NMR (CDCl$_3$) δ7.86–7.80 (m, 2H), 7.72 (s, 1H), 7.66–7.59 (m, 2H), 7.45–7.40 (m, 2H), 7.32–7.22 (m, 3H) ppm.

Preparation of Compound 175

To a solution of the product of step 1 (0.045 g, 0.12 mmol) in dimethylsulfoxide (1.0 mL) was added 3-chlorobenzylamine (0.018 g, 0.13 mmol). The reaction mixture was heated to 70° C. and stirred for 14 hours. The cooled mixture was diluted with water (15 mL) and extracted with ethyl acetate (2×10 mL). The combined organic phases were washed with 10% aqueous hydrochloric acid solution and brine, dried (magnesium sulfate), filtered and concentrated to provide a yellow solid. Flash chromatography over silica (hexanes/ethyl acetate) provided 0.025 g (49%) of the product as a white solid: 1H NMR (DMSO-$d_6$) d 10.8 (br s, 1H), 7.81–7.78 (m, 2H), 7.60–7.53 (m, 3H), 7.38–7.25 (m, 4H), 7.09 (s, 1H), and 4.34 (d, J=5.3 Hz, 2H) ppm.

The compounds presented in Tables 1, 2 and 3 were prepared by the methods set forth in Examples 1–14.

TABLE 1

Compounds of Formula I.  (I)

$$\begin{array}{c} R_1 \quad R_2 \\ \diagup \quad \diagdown R_3 \\ N \quad \diagup \\ \diagdown N \diagup \quad =O \\ R_4 \end{array}$$

| Cmpd No. | Ex. No. | $R_1$ | $R_2$, $R_3$ | $R_4$ |
| --- | --- | --- | --- | --- |
| 1 | 1 | Ph | H, H | 3,5-DiClPh |
| 2 | 1 | Ph | H, H | 3,4-DiClPh |
| 3 | 2 | Ph | =CH((4-OCH$_3$)Ph) | 3,5-DiClPh |
| 4 | 1 | Ph | CH$_3$, CH$_3$ | 3,5-DiClPh |
| 5 | 1 | CH$_3$ | H, H | 3,5-DiClPh |
| 6 | 1 | 4-(CH$_3$)Ph | H, H | 3,5-DiClPh |
| 7 | 1 | 2-FPh | H, H | 3,5-DiClPh |
| 8 | 1 | Cyclohexyl | H, H | 3,5-DiClPh |
| 9 | 3 | Ph | =CHN(CH$_3$)$_2$ | 3,5-DiClPh |
| 10 | 1 | CH$_2$CH$_2$CH$_3$ | H, H | 3,5-DiClPh |
| 11 | 1 | CH$_3$ | CH$_3$, H | 3,5-DiClPh |
| 12 | 1 | | —CH$_2$CH$_2$CH$_2$— | 3,5-DiClPh |
| 13 | 1 | CH(CH$_3$)$_2$ | H, H | 3,5-DiClPh |
| 14 | 1 | CF$_3$ | H, H | 3,5-DiClPh |
| 15 | 1 | 3-FPh | H, H | 3,5-DiClPh |
| 16 | 1 | 4-FPh | H, H | 3,5-DiClPh |
| 17 | 1 | CH$_2$CH$_3$ | H, H | 3,5-DiClPh |
| 18 | 1 | | —CH$_2$CH$_2$CH$_2$CH$_2$— | 3,5-DiClPh |
| 19 | 2 | Ph | —CH(4-Pyridyl) | 3,5-DiClPh |
| 20 | 1 | CH$_3$ | CH$_2$CH$_3$,H | 3,5-DiClPh |
| 21 | 1 | CH$_3$ | CH$_2$Ph,H | 3,5-DiClPh |
| 22 | 5 | Ph | =C(CH$_3$)$_2$ | 3,5-DiClPh |
| 23 | 4 | Ph | =N—OH | 3,5-DiClPh |
| 24 | 2 | Ph | =CHPh(2-COOH) | 3,5-DiClPh |
| 25 | 2 | Ph | =CH(C=O)CH$_3$ | 3,5-DiClPh |
| 26 | 2 | Ph | =CH(C=O)Ph | 3,5-DiClPh |
| 27 | 2 | Ph | =CH((4-N(CH$_2$CH$_3$)$_2$)Ph) | 3,5-DiClPh |
| 28 | 2 | Ph | =CH((4-OCH$_2$CH$_2$CH$_2$N(CH$_3$)$_2$)Ph) | 3,5-DiClPh |
| 29 | 2 | Ph | =CH(2-Pyridyl) | 3,5-DiClPh |
| 30 | 2 | Ph | =CH(3-Pyridyl) | 3,5-DiClPh |
| 31 | 5 | Ph | =CH(4-Piperidinyl(N—CH$_3$)) | 3,5-DiClPh |
| 32 | 2 | Ph | =CH(2-Pyrrolyl(N—CH$_3$)) | 3,5-DiClPh |
| 33 | 2 | Ph | =CH(3-Thiophene-yl) | 3,5-DiClPh |
| 34 | 2 | Ph | =CH(3-Furanyl) | 3,5-DiClPh |
| 35 | 2 | Ph | =CH(2-Furanyl) | 3,5-DiClPh |
| 36 | 2 | Ph | =CH(2-Thiophene-yl) | 3,5-DiClPh |
| 37 | 2 | Ph | =CH(2-Thiazolyl) | 3,5-DiClPh |
| 38 | 2 | Ph | =CH((4-CH$_3$S)Ph) | 3,5-DiClPh |
| 39 | 2 | Ph | =CH(3-Indolyl) | 3,5-DiClPh |
| 40 | 5 | Ph | =CH(4-Thiopyranyl) | 3,5-DiClPh |
| 41 | 5 | Ph | =(4-Piperidinyl(N—CO$_2$CH$_2$CH$_3$)) | 3,5-DiClPh |
| 42 | 5 | Ph | =(3-(2-oxo)-indolinyl) | 3,5-DiClPh |
| 43 | 2 | Ph | =CH(3-Indolyl(N—CH$_3$)) | 3,5-DiClPh |
| 44 | 2 | Ph | =CH((2-COOMe)Ph) | 3,5-DiClPh |
| 45 | 2 | Ph | —CH(2-Furanyl(2-CH$_2$OH)) | 3,5-DiClPh |
| 46 | 2 | Ph | =CH(CO$_2$H) | 3,5-DiClPh |
| 47 | 1 | Ph | H, H | 3,5-Di(CF$_3$)Ph |
| 48 | 1 | 2-Pyridyl | H, H | 3,5-DiClPh |
| 49 | 6 | Ph | (C=O)((4-OCH$_3$)Ph), H | 3,5-DiClPh |
| 50 | 6 | Ph | (C=O)-(2-pyridyl), H | 3,5-DiClPh |
| 51 | 2 | Ph | =CH((3-CO$_2$H)Ph) | 3,5-DiClPh |
| 52 | 2 | Ph | =CH((4-CO$_2$H)Ph) | 3,5-DiClPh |
| 53 | 1 | 3-Pyridyl | H, H | 3,5-DiClPh |
| 54 | 2 | CH$_2$CH$_3$ | =CH(3-Pyridyl) | 3,5-DiClPh |
| 55 | 2 | CH$_2$CH$_3$ | =CH(2-Furanyl) | 3,5-DiClPh |
| 56 | 5 | CH$_2$CH$_3$ | =(3-(2-oxo)-indolinyl) | 3,5-DiClPh |
| 57 | 2 | CH$_2$CH$_3$ | =CH(CO$_2$H) | 3,5-DiClPh |
| 58 | 2 | CH$_2$CH$_3$ | =CH((3-CO$_2$H)Ph) | 3,5-DiClPh |
| 59 | 2 | CH$_2$CH$_3$ | =CH((4-CO$_2$H)Ph) | 3,5-DiClPh |
| 60 | 4 | CH$_2$CH$_3$ | =N—OH | 3,5-DiClPh |
| 61 | 2 | CH$_2$CH$_3$ | =CHCH$_2$CH$_2$CO$_2$H | 3,5-DiClPh |
| 62 | 5 | CO$_2$CH$_2$CH$_3$ | =CH(3-(2-oxo)-indolinyl) | 3,5-DiClPh |

TABLE 1-continued

Compounds of Formula I. (I)

$$\text{Formula I structure with } R_1, R_2, R_3, R_4$$

| Cmpd No. | Ex. No. | $R_1$ | $R_2, R_3$ | $R_4$ |
|---|---|---|---|---|
| 63 | 2 | $CO_2CH_2CH_3$ | =CH((4-$CO_2$H)Ph) | 3,5-DiClPh |
| 64 | 2 | $CO_2CH_2CH_3$ | =CH($CO_2$H) | 3,5-DiClPh |
| 65 | 1 | $CH_2$Ph | H, H | 3,5-DiClPh |
| 66 | 1 | Ph | $CH_2CH_2$(2-Pyridyl), H | 3,5-DiClPh |
| 67 | 1 | $CO_2CH_2CH_3$ | H, H | 3,5-DiClPh |
| 68 | 2 | $CH_2CH_3$ | =CH(3-(4-$CH_3$-piperazine-C=O)Ph) | 3,5-DiClPh |
| 69 | 2 | $CH_2CH_3$ | =CH(3-(morpholine-4-C=O)Ph) | 3,5-DiClPh |
| 70 | 2 | $CH_2CH_3$ | =CH(3-(C=ONHCH2CH2OH)Ph) | 3,5-DiClPh |

TABLE 2

Compounds of Formula II (II)

$$\text{Formula II structure with } R_5, R_8, R_6, R_7$$

| Cmpd No. | Ex. No. | $R_7$ | $R_5$ | $R_8$ | $R_6$ |
|---|---|---|---|---|---|
| 71 | 7 | 4-($CF_3$)Ph | H | Ph | 3,5-Di($CF_3$)Ph |
| 72 | 7 | 4-($CF_3$)Ph | t-Bu | H | 3,5-Di($CF_3$)Ph |
| 73 | 7 | 4-($CF_3$)Ph | t-Bu | H | 3,5-DiClPh |
| 74 | 7 | 4-($CF_3$)Ph | Bn | H | 3,5-Di($CF_3$)Ph |
| 75 | 7 | 4-($CF_3$)Ph | Ph | H | 3-($CF_3$)-4-ClPh |
| 76 | 7 | 4-($CF_3$)Ph | Ph | H | 3,5-Di($CF_3$)Ph |
| 77 | 7 | 4-($CF_3$)Ph | Ph | H | 3,5-DiClPh |
| 78 | 7 | 4-($CF_3$)Ph | 3-ClPh | H | 3,5-Di($CF_3$)Ph |
| 79 | 7 | 4-($CF_3$)Ph | 4-Clph | H | 3,5-Di($CF_3$)Ph |
| 80 | 7 | 4-($CF_3$)Ph | 3-($CF_3$)Ph | H | 3,5-Di($CF_3$)Ph |
| 81 | 7 | 4-($CF_3$)Ph | 4-($OCF_3$)Ph | H | 3,5-Di($CF_3$)Ph |
| 82 | 7 | 4-($CF_3$)Ph | 4-($OCH_3$)Ph | H | 3,5-Di($CF_3$)Ph |
| 83 | 7 | 4-($CF_3$)Ph | 2-thiophene | H | 3,5-Di($CF_3$)Ph |
| 84 | 7 | 4-($CF_3$)Ph | 2-thiophene | H | 3,5-DiClPh |
| 85 | 8 | 4-($CF_3$)Ph | 2-pyridyl | H | 3,5-Di($CF_3$)Ph |
| 86 | 8 | 4-($CF_3$)Ph | 3-pyridyl | H | 3,5-Di($CF_3$)Ph |
| 87 | 8 | 4-($CF_3$)Ph | 4-pyridyl | H | 3,5-Di($CF_3$)Ph |
| 88 | 8 | 4-($CF_3$)Ph | 4-((4-morpholino)$CH_2$)Ph | H | 3,5-Di($CF_3$)Ph |
| 89 | 8 | 4-($CF_3$)Ph | (4-morpholino)$CH_2$— | H | 3,5-Di($CF_3$)Ph |
| 90 | 8 | 4-($CF_3$)Ph | (($CH_3$)$_2$N)$CH_2$— | H | 3,5-Di($CF_3$)Ph |
| 91 | 7 | 4-ClPh | Ph | H | 3,5-DiClPh |
| 92 | 10 | 4-BrPh | H | H | 3,5-Di($CF_3$)Ph |
| 93 | 10 | 4-BrPh | H | H | 3,5-DiClPh |
| 94 | 10 | 4-BrPh | H | $CO_2$Et | 3,5-Di($CF_3$)Ph |
| 95 | 9 | 4-BrPh | $CH_3$ | H | 3,5-Di($CF_3$)Ph |
| 96 | 9 | 4-BrPh | $CH_3$ | H | 3,5-DiClPh |
| 97 | 11 | 4-BrPh | $CH_3$ | Br | 3,5-Di($CF_3$)Ph |
| 98 | 7 | 4-BrPh | $CO_2$Et | H | 3,5-Di($CF_3$)Ph |
| 99 | 12 | 4-BrPh | $HOCH_2$— | H | 3,5-Di($CF_3$)Ph |
| 100 | 7 | 4-BrPh | t-Bu | H | 3,5-DiClPh |
| 101 | 7 | 4-BrPh | t-Bu | H | 3,5-Di($CF_3$)Ph |
| 102 | 8 | 4-BrPh | ($CH_3OCH_2CH_2$)$_2NCH_2$— | H | 3,5-DiClPh |
| 103 | 8 | 4-BrPh | ($CH_3OCH_2CH_2$)$_2NCH_2$— | H | 3,5-Di($CF_3$)Ph |
| 104 | 8 | 4-BrPh | ($HOCH_2CH_2$)$_2NCH_2$— | H | 3,5-Di($CF_3$)Ph |
| 105 | 7 | 4-BrPh | —$CH_2CH_2CH_2CH_2$— | | 3,5-DiClPh |
| 106 | 7 | 4-BrPh | —$CH_2CH_2CH_2CH_2$— | | 3,5-Di($CF_3$)Ph |

TABLE 2-continued

Compounds of Formula II (II)

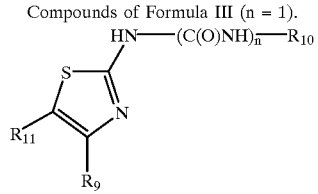

| Cmpd No. | Ex. No. | $R_7$ | $R_5$ | $R_8$ | $R_6$ |
|---|---|---|---|---|---|
| 107 | 7 | 4-BrPh | Ph | H | 3,5-DiClPh |
| 108 | 8 | 4-BrPh | 2-thiophene | H | 3,5-DiClPh |
| 109 | 8 | 4-BrPh | 2-thiophene | H | 3,5-Di(CF$_3$)Ph |
| 110 | 7 | 4-BrPh | 3-thiophene | H | 3,5-DiClPh |
| 111 | 7 | 4-BrPh | 3-thiophene | H | 3,5-Di(CF$_3$)Ph |
| 112 | 7 | 4-BrPh | 2-furyl | H | 3,5-DiClPh |
| 113 | 7 | 4-BrPh | 2-furyl | H | 3,5-Di(CF$_3$)Ph |
| 114 | 7 | 4-BrPh | 5-CH$_3$-isoxazol-3-yl | H | 3,5-DiClPh |
| 115 | 7 | 4-BrPh | 5-CH$_3$-isoxazol-3-yl | H | 3,5-Di(CF$_3$)Ph |
| 116 | 8 | 4-BrPh | 3-pyridyl | H | 3,5-DiClPh |
| 117 | 8 | 4-BrPh | 3-pyridyl | H | 3,5-Di(CF$_3$)Ph |
| 118 | 8 | 4-BrPh | 4-pyridyl | H | 3,5-DiClPh |
| 119 | 8 | 4-BrPh | 4-pyridyl | H | 3,5-Di(CF$_3$)Ph |
| 120 | 7 | CF$_3$CH$_2$ | Ph | H | 3,5-DiClPh |
| 121 | 7 | CF$_3$CH$_2$ | Ph | H | 3,5-Di(CF$_3$)Ph |

TABLE 3

Compounds of Formula III (n = 1). (III)

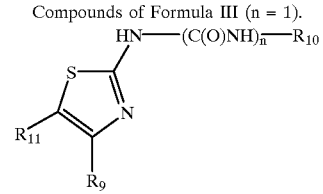

| Cmpd No. | Ex. No. | $R_{11}$ | $R_9$ | $R_{10}$ |
|---|---|---|---|---|
| 122 | 13 | CH$_3$ | H | 3,5-Di(CF$_3$)Ph |
| 123 | 13 | CH$_3$ | CH$_3$ | 3,5-Di(CF$_3$)Ph |
| 124 | 13 | H | t-Bu | 3,5-Di(CF$_3$)Ph |
| 125 | 13 | H | HO(CH$_2$)$_3$ | 3,5-Di(CF$_3$)Ph |
| 126 | 13 | H | CH$_2$=CH(CH$_2$)$_2$ | 3,5-Di(CF$_3$)Ph |
| 127 | 13 | H | HO$_2$CCH$_2$ | 3,5-Di(CF$_3$)Ph |
| 128 | 13 | CH$_3$ | CH$_3$CH$_2$OC(O) | 3,5-Di(CF$_3$)Ph |
| 129 | 13 | H | CH$_3$CH$_2$OC(O)C(O) | 3,5-Di(CF$_3$)Ph |
| 130 | 13 | H | PhCH$_2$ | 3,5-Di(CF$_3$)Ph |
| 131 | 13 | H | Ph(CH$_2$)$_2$ | 3,5-Di(CF$_3$)Ph |
| 132 | 13 | H | Ph | 3,5-Di(CF$_3$)Ph |
| 133 | 13 | H | 2-(OCH$_3$)Ph | 3,5-Di(CF$_3$)Ph |
| 134 | 13 | H | 3-(OCH$_3$)Ph | 3,5-Di(CF$_3$)Ph |
| 135 | 13 | H | 3-FPh | 3,5-Di(CF$_3$)Ph |
| 136 | 13 | H | 4-BrPh | 3,5-Di(CF$_3$)Ph |
| 137 | 13 | CH$_3$ | 4-BrPh | 3,5-Di(CF$_3$)Ph |
| 138 | 13 | H | 4-ClPh | 3,5-Di(CF$_3$)Ph |
| 139 | 13 | H | 4-FPh | 3,5-Di(CF$_3$)Ph |
| 140 | 13 | H | 4-(CH$_3$)Ph | 3,5-Di(CF$_3$)Ph |
| 141 | 13 | H | 4-(OCH$_3$)Ph | 3,5-Di(CF$_3$)Ph |
| 142 | 13 | H | 4-(OCHF$_2$)Ph | 3,5-Di(CF$_3$)Ph |
| 143 | 13 | H | 4-(CF$_3$)Ph | 3,5-Di(CF$_3$)Ph |
| 144 | 13 | H | 4-(CN)Ph | 3,5-Di(CF$_3$)Ph |
| 145 | 13 | H | 4-(HOCH$_2$)Ph | 3,5-Di(CF$_3$)Ph |
| 146 | 13 | H | 4-(HO(CH$_2$)$_2$)Ph | 3,5-Di(CF$_3$)Ph |
| 147 | 13 | H | 4-(Ph)Ph | 3,5-Di(CF$_3$)Ph |
| 148 | 13 | H | 2,4-DiClPh | 3,5-Di(CF$_3$)Ph |
| 149 | 13 | H | 2,4-DiFPh | 3,5-Di(CF$_3$)Ph |
| 150 | 13 | H | 3,4-DiClPh | 3,5-Di(CF$_3$)Ph |
| 151 | 13 | H | 3,4-DiFPh | 3,5-Di(CF$_3$)Ph |
| 152 | 13 | H | 3-(CH$_3$)-4-FPh | 3,5-Di(CF$_3$)Ph |
| 153 | 13 | H | 2-Naphthyl | 3,5-Di(CF$_3$)Ph |
| 154 | 13 | H | 3-(HOCH$_2$)-isoxazol-5-yl | 3,5-Di(CF$_3$)Ph |
| 155 | 13 | H | Thiophen-2-yl | 3,5-Di(CF$_3$)Ph |
| 156 | 13 | | —CHCHCHCH— | 3,5-Di(CF$_3$)Ph |
| 157 | 13 | H | 4-(5-Cl-3-CH$_3$-benzo[b]thiophen-2-yl) | 3,5-Di(CF$_3$)Ph |
| 158 | 13 | | —CH$_2$C(O(CH$_2$)$_2$O)CH$_2$CH$_2$— | 3,5-Di(CF$_3$)Ph |
| 159 | 14 | H | 4-BrPh | 3-BrPh |
| 160 | 13 | H | 3,4-DiFPh | 4-(OCHF$_2$)Ph |
| 161 | 13 | H | 3,4-DiFPh | 4-(SCF$_3$)Ph |
| 162 | 13 | H | 4-ClPh | 2-(CF$_3$)-4-BrPh |
| 163 | 14 | H | 4-ClPh | 3,5-DiClPh |
| 164 | 13 | H | 3,4-DiFPh | 3,5-DiClPh |
| 165 | 14 | H | 3-FPh | 3-(CF$_3$)-4-FPh |
| 166 | 13 | H | 4-BrPh | 3-(CF$_3$)-4-FPh |
| 167 | 13 | H | 4-Clph | 3-(CF$_3$)-4-FPh |
| 168 | 13 | H | 3,4-DiFPh | 3-(CF$_3$)-4-FPh |
| 169 | 13 | H | 3-(CH$_3$)-4-FPh | 3-(CF$_3$)-4-FPh |
| 170 | 13 | H | 4-ClPh | 2,4,5-TriClPh |
| 171 | 13 | H | 4-ClPh | 2,4,6-TriClPh |
| 172 | 13 | H | t-Bu | (3-ClPh)CH$_2$ |
| 173 | 13 | H | Cyclopentyl | (3-ClPh)CH$_2$ |
| 174 | 13 | H | 3-FPh | (3-ClPh)CH$_2$ |
| 175 | 14 | H | 4-BrPh | (3-ClPh)CH$_2$ |
| 176 | 13 | H | 4-(CF$_3$)Ph | (3-ClPh)CH$_2$ |
| 177 | 13 | H | 2,4-DiClPh | (3-ClPh)CH$_2$ |
| 178 | 13 | H | 2,4-DiFPh | (3-ClPh)CH$_2$ |
| 179 | 13 | H | 3,4-DiClPh | (3-ClPh)CH$_2$ |
| 180 | 13 | H | 3-(CH$_3$)-4-FPh | (3-ClPh)CH$_2$ |

TABLE 3-continued

Compounds of Formula III (n = 1). (III)

HN—(C(O)NH)$_n$—R$_{10}$, with thiazole ring bearing R$_{11}$ and R$_9$

| Cmpd No. | Ex. No. | R$_{11}$ | R$_9$ | R$_{10}$ |
|---|---|---|---|---|
| 181 | 14 | H | 4-BrPh | (3,4-DiClPh)CH$_2$ |
| 182 | 13 | H | 3,4-DiFPh | (3,4-DiClPh)CH$_2$ |
| 183 | 14 | H | 4-BrPh | PhCH(OH)CH(CH$_3$) |

Example 15

In vitro Testing of Compounds

Minimal inhibitory concentrations (MICs) for *Staphylococcus aureus* bacteria (ATCC 9604 SV) were determined by broth microdilution methodology following National Committee for Clinical Laboratory Standards. In the MIC determinations, the compounds were incorporated into Mueller-Hinton broth (Becton Dickinson Microbiology systems, Cockeyville, Md.) at a series of concentrations. After the test organism was grown overnight in TB broth, the broths were adjusted to the turbidity equivalent to 0.05 McFarland standard. The suspensions were diluted twenty-fold into the broth containing the compounds. After 24 hours cultivation at 37° C., the MICs were determined as the lowest concentration of antimicrobial agent that completely inhibits growth of the organism in the microdilution wells as detected by the unaided eye. In the IC$_{50}$ determination, the method was modified to allow the rapid growth of the organisms. The inoculum suspensions were adjusted to 0.1 McFarland standard and then diluted two-fold into the wells containing TB broth and the compounds. After three to five hours incubation at 37° C., the turbidity was measured at 550 nm and inhibitory activity was defined as the concentration of antimicrobial agent that inhibits 50% growth of the organism in the microdilution wells.

Example 16

In Vivo Assays

Ten male ICR mice weighing 20 grams were inoculated intraperitoneally with an LD$_{90-100}$ dose (2–3×10$^7$ CFU/mouse) of methicillin-resistant *Staphylococcus aureus* (ATCC 33591) in brain-heart infusion broth containing 5% mucin. Compounds were suspended in a vehicle containing 1% cremophore EL (Sigma) in normal saline and were administered subcutaneously in a volume of 0.4 ml per mouse either 1 hour following bacterial inoculation or 1 and 5 hours post inoculation. Animals receiving two doses of drug were injected subcutaneously in the hindquarter one hour post-innoculation and in the neck area, 5 hours post-innoculation. Deaths occurring during the subsequent 7 days are recorded. Mortality and % survivor endpoints are calculated.

TABLE 4

In vitro and in vivo antibacterial activity of compounds of Formulas I, II and III.

| Cmpd. No. | IC$_{50}$ (μM) | MIC (μg/mL) | In Vivo, single dose (% of mice rescued) | In Vivo, double dose (% of mice rescued) |
|---|---|---|---|---|
| 1 | 0.540 | 0.122 | NT[a] | 0% @ 2 × 2 mg/kg |
|   |       |       |       | 25% @ 2 × 20 mg/kg |
| 2 | 0.449 | 1.91 | NT | 0% @ 2 × 2 mg/kg |
|   |       |       |       | 0% @ 2 × 20 mg/kg |
| 3 | 0.985 | 1.30 | NT | 25% @ 2 × 2 mg/kg |
|   |       |       |       | 25% @ 2 × 20 mg/kg |
| 4 | NT | >8.33 | NT | NT |
| 5 | NT | 6.08 | NT | NT |
| 6 | NT | >7.98 | NT | NT |
| 7 | NT | >8.08 | NT | NT |
| 8 | NT | >7.78 | NT | NT |
| 9 | NT | >9.01 | NT | NT |
| 10 | NT | 0.813 | NT | 0% @ 2 × 2 mg/kg |
|   |    |       |    | 0% @ 2 × 20 mg/kg |
| 11 | NT | >6.43 | NT | NT |
| 12 | NT | >6.73 | NT | NT |
| 13 | NT | >6.78 | NT | NT |
| 14 | NT | 3.56 | NT | NT |
| 15 | NT | 0.485 | NT | 0% @ 2 × 2 mg/kg |
|   |    |       |    | 0% @ 2 × 20 mg/kg |
| 16 | NT | 0.485 | NT | 0% @ 2 × 2 mg/kg |
|   |    |       |    | 25% @ 2 × 20 mg/kg |
| 17 | NT | 1.54 | NT | 12.5% @ 2 × 2 mg/kg |
|   |    |       |    | 25% @ 2 × 20 mg/kg |
| 18 | NT | >7.08 | NT | NT |
| 19 | NT | 1.15 | NT | 0% @ 2 × 2 mg/kg |
|   |    |       |    | 25% @ 2 × 20 mg/kg |
| 20 | NT | >6.78 | NT | NT |
| 21 | NT | 8.33 | NT | NT |
| 22 | NT | 0.518 | NT | 0% @ 2 × 2 mg/kg |
|   |    |       |    | 25% @ 2 × 20 mg/kg |
| 23 | NT | 8.35 | NT | 0% @ 2 × 2 mg/kg |
|   |    |       |    | 25% @ 2 × 20 mg/kg |
| 24 | NT | 1.35 | NT | 0% @ 2 × 2 mg/kg |

TABLE 4-continued

In vitro and in vivo antibacterial activity of compounds of Formulas I, II and III.

| Cmpd. No. | IC$_{50}$ ($\mu$M) | MIC ($\mu$g/mL) | In Vivo, single dose (% of mice rescued) | In Vivo, double dose (% of mice rescued) |
|---|---|---|---|---|
| 25 | NT | 3.12 | NT | 0% @ 2 × 20 mg/kg<br>0% @ 2 × 2 mg/kg |
| 26 | NT | >12.5 | NT | 0% @ 2 × 20 mg/kg |
| 27 | NT | >12.5 | NT | NT |
| 28 | NT | >12.5 | NT | NT |
| 29 | NT | 12.5 | NT | NT |
| 30 | NT | 1.20 | NT | 0% @ 2 × 2 mg/kg<br>0% @ 2 × 20 mg/kg |
| 31 | NT | 5.00 | NT | 0% @ 2 × 2 mg/kg<br>0% @ 2 × 20 mg/kg |
| 32 | NT | 0.320 | NT | NT |
| 33 | NT | 5.00 | NT | 25% @ 2 × 2 mg/kg<br>0% @ 2 × 20 mg/kg |
| 34 | NT | 2.40 | NT | 25% @ 2 × 2 mg/kg<br>25% @ 2 × 20 mg/kg |
| 35 | NT | >12.5 | NT | NT |
| 36 | NT | 12.5 | NT | NT |
| 37 | NT | 12.5 | NT | NT |
| 38 | NT | 6.25 | NT | NT |
| 39 | NT | >10.0 | NT | NT |
| 40 | NT | 0.320 | NT | NT |
| 41 | NT | 12.5 | NT | NT |
| 42 | NT | 1.20 | NT | 0% @ 2 × 2 mg/kg<br>0% @ 2 × 20 mg/kg |
| 43 | NT | 0.400 | NT | NT |
| 44 | NT | 12.5 | NT | NT |
| 45 | NT | 2.40 | NT | 0% @ 2 × 2 mg/kg<br>0% @ 2 × 20 mg/kg |
| 46 | NT | 1.50 | NT | 0% @ 2 × 2 mg/kg<br>0% @ 2 × 20 mg/kg |
| 47 | NT | 2.33 | NT | NT |
| 48 | NT | >7.65 | NT | NT |
| 49 | NT | 10.0 | NT | 0% @ 2 × 2 mg/kg<br>25% @ 2 × 20 mg/kg |
| 50 | NT | 10.3 | NT | 0% @ 2 × 2 mg/kg<br>0% @ 2 × 20 mg/kg |
| 51 | NT | 1.31 | NT | 25% @ 2 × 2 mg/kg<br>25% @ 2 × 20 mg/kg |
| 52 | NT | 0.656 | NT | 0% @ 2 × 2 mg/kg<br>0% @ 2 × 20 mg/kg |
| 53 | NT | 7.65 | NT | NT |
| 54 | NT | 0.750 | NT | 0% @ 2 × 2 mg/kg<br>12.5% @ 2 × 20 mg/kg |
| 55 | NT | 1.50 | NT | 0% @ 2 × 2 mg/kg<br>25% @ 2 × 20 mg/kg |
| 56 | NT | 1.50 | NT | 0% @ 2 × 2 mg/kg<br>0% @ 2 × 20 mg/kg |
| 57 | NT | 6.25 | NT | 0% @ 2 × 2 mg/kg<br>0% @ 2 × 20 mg/kg |
| 58 | NT | 6.25 | NT | 25% @ 2 × 2 mg/kg<br>12.5% @ 2 × 20 mg/kg |
| 59 | NT | 0.400 | NT | 12.5% @ 2 × 2 mg/kg<br>12.5% @ 2 × 20 mg/kg |
| 60 | NT | 7.15 | NT | NT |
| 61 | NT | 8.53 | NT | NT |
| 62 | NT | 12.5 | NT | NT |
| 63 | NT | 12.5 | NT | NT |
| 64 | NT | 6.25 | NT | NT |
| 65 | NT | 0.958 | NT | 0% @ 2 × 2 mg/kg<br>0% @ 2 × 20 mg/kg |
| 66 | NT | 5.13 | NT | 25% @ 2 × 2 mg/kg<br>0% @ 2 × 20 mg/kg |
| 67 | NT | 3.76 | NT | NT |
| 68 | NT | 11.8 | NT | NT |
| 69 | NT | 11.5 | NT | NT |
| 70 | NT | 5.40 | NT | NT |
| 71 | 0.330 | NT | NT | NT |
| 72 | 0.058 | 0.808 | 0% @ 2 mg/kg<br>0% @ 20 mg/kg | NT |
| 73 | 0.083 | NT | 0% @ 2 mg/kg<br>0% @ 20 mg/kg | NT |
| 74 | 0.127 | 3.43 | NT | NT |
| 75 | 0.096 | <0.787 | NT | NT |

TABLE 4-continued

In vitro and in vivo antibacterial activity of compounds of Formulas I, II and III.

| Cmpd. No. | IC$_{50}$ ($\mu$M) | MIC ($\mu$g/mL) | In Vivo, single dose (% of mice rescued) | In Vivo, double dose (% of mice rescued) |
|---|---|---|---|---|
| 76 | 0.054 | <0.838 | 0% @ 2 mg/kg<br>0% @ 20 mg/kg | NT |
| 77 | 0.081 | 12.3 | 0% @ 2 mg/kg<br>12.5% @ 20 mg/kg | NT |
| 78 | 0.206 | NT | NT | NT |
| 79 | 0.126 | NT | NT | NT |
| 80 | 0.539 | NT | NT | NT |
| 81 | 0.159 | NT | NT | NT |
| 82 | 0.149 | NT | NT | NT |
| 83 | 0.071 | 0.847 | 0% @ 2 mg/kg<br>25% @ 20 mg/kg | NT |
| 84 | 0.134 | 6.22 | 0% @ 2 mg/kg<br>0% @ 20 mg/kg | NT |
| 85 | 0.359 | NT | NT | NT |
| 86 | 0.205 | 1.68 | 0% @ 2 mg/kg<br>0% @ 20 mg/kg | NT |
| 87 | 0.214 | 1.68 | 25% @ 2 mg/kg<br>25% @ 20 mg/kg | 0% @ 2 × 2 mg/kg<br>17% @ 2 × 20 mg/kg |
| 88 | 1.48 | >32.9 | NT | NT |
| 89 | 0.216 | >29.1 | 0% @ 2 mg/kg<br>0% @ 20 mg/kg | NT |
| 90 | 4.40 | 13.5 | NT | NT |
| 91 | 0.148 | >22.9 | 0% @ 2 mg/kg<br>0% @ 20 mg/kg | |
| 92 | 0.209 | <0.740 | 0% @ 2 mg/kg<br>0% @ 20 mg/kg | NT |
| 93 | 0.138 | <0.639 | 0% @ 2 mg/kg<br>25% @ 20 mg/kg | NT |
| 94 | 0.261 | <0.848 | 0% @ 2 mg/kg<br>0% @ 20 mg/kg | NT |
| 95 | 0.268 | <0.761 | 25% @ 2 mg/kg<br>25% @ 20 mg/kg | NT |
| 96 | 0.967 | >22.0 | 0% @ 2 mg/kg<br>25% @ 20 mg/kg | NT |
| 97 | 0.107 | >29.3 | NT | NT |
| 98 | 3.10 | >14.1 | NT | 0% @ 2 × 2 mg/kg<br>33% @ 2 × 20 mg/kg |
| 99 | 4.24 | 6.54 | NT | 33% @ 2 × 2 mg/kg<br>33% @ 2 × 20 mg/kg |
| 100 | 0.132 | <0.723 | 0% @ 2 mg/kg<br>0% @ 20 mg/kg | NT |
| 101 | 0.143 | <0.824 | 0% @ 2 mg/kg<br>0% @ 20 mg/kg | NT |
| 102 | 3.52 | 28.6 | 0% @ 2 mg/kg<br>25% @ 20 mg/kg | NT |
| 103 | 1.56 | 16.0 | 25% @ 2 mg/kg<br>25% @ 20 mg/kg | 0% @ 2 × 2 mg/kg<br>33% @ 2 × 20 mg/kg |
| 104 | 6.80 | 15.3 | NT | 17% @ 2 × 2 mg/kg<br>17% @ 2 × 20 mg/kg |
| 105 | 3.21 | >24.0 | NT | NT |
| 106 | 0.459 | >27.4 | NT | NT |
| 107 | 0.121 | 6.28 | 25% @ 2 mg/kg<br>12.5% @ 20 mg/kg<br>10% @ 40 mg/kg<br>10% @ 80 mg/kg<br>5% @ 160 mg/kg | 0% @ 2 × 2 mg/kg<br>17% @ 2 × 20 mg/kg |
| 108 | 0.194 | >25.4 | 0% @ 2 mg/kg<br>0% @ 20 mg/kg | NT |
| 109 | 0.155 | <0.863 | 25% @ 2 mg/kg<br>25% @ 20 mg/kg | NT |
| 110 | 0.164 | 25.4 | 0% @ 2 mg/kg<br>0% @ 20 mg/kg | NT |
| 111 | 0.126 | <0.863 | 0% @ 2 mg/kg<br>0% @ 20 mg/kg | NT |
| 112 | 0.232 | 6.15 | 0% @ 2 mg/kg<br>0% @ 20 mg/kg | NT |
| 113 | 0.152 | <0.839 | 25% @ 2 mg/kg<br>0% @ 20 mg/kg | NT |
| 114 | 1.63 | NT | NT | NT |
| 115 | 0.402 | 1.72 | NT | NT |
| 116 | 0.391 | 3.02 | 0% @ 2 mg/kg<br>0% @ 20 mg/kg | NT |
| 117 | 0.238 | 3.42 | 25% @ 2 mg/kg<br>0% @ 20 mg/kg | NT |

TABLE 4-continued

In vitro and in vivo antibacterial activity of compounds of Formulas I, II and III.

| Cmpd. No. | IC$_{50}$ ($\mu$M) | MIC ($\mu$g/mL) | In Vivo, single dose (% of mice rescued) | In Vivo, double dose (% of mice rescued) |
|---|---|---|---|---|
| 118 | 0.239 | 0.755 | NT | NT |
| 119 | 0.163 | 0.855 | NT | NT |
| 120 | 0.291 | >21.5 | 0% @ 2 mg/kg | NT |
|  |  |  | 0% @ 20 mg/kg |  |
| 121 | 0.084 | <1.49 | 0% @ 2 mg/kg | NT |
|  |  |  | 0% @ 20 mg/kg |  |
| 122 | 2.72 | >18.5 | NT | NT |
| 123 | 0.520 | 1.15 | NT | NT |
| 124 | 0.513 | NT | NT | NT |
| 125 | 2.07 | NT | NT | NT |
| 126 | 0.612 | 10.2 | NT | NT |
| 127 | 29.3 | >20.7 | NT | NT |
| 128 | 0.510 | NT | 0% @ 2 mg/kg | NT |
|  |  |  | 0% @ 20 mg/kg |  |
| 129 | 0.944 | 11.4 | NT | NT |
| 130 | 0.275 | 1.34 | NT | NT |
| 131 | 0.367 | 23.4 | NT | NT |
| 132 | 0.970 | NT | NT | NT |
| 133 | 4.63 | NT | NT | NT |
| 134 | 4.52 | NT | NT | NT |
| 135 | 0.107 | 1.35 | NT | NT |
| 136 | 0.133 | NT | NT | NT |
| 137 | 0.838 | NT | NT | NT |
| 138 | 0.100 | NT | NT | NT |
| 139 | 0.100 | NT | 0% @ 2 mg/kg | NT |
|  |  |  | 0% @ 20 mg/kg |  |
| 140 | 0.653 | NT | NT | NT |
| 141 | 1.36 | NT | NT | NT |
| 142 | 0.235 | 6.22 | NT | NT |
| 143 | 0.129 | 1.40 | NT | NT |
| 144 | 0.337 | NT | NT | NT |
| 145 | 3.74 | >23.1 | NT | NT |
| 146 | 1.61 | 2.71 | NT | NT |
| 147 | 0.799 | NT | NT | NT |
| 148 | 0.40 | NT | NT | NT |
| 149 | 0.879 | NT | NT | NT |
| 150 | 0.410 | NT | NT | NT |
| 151 | 0.132 | 1.40 | 0% @ 2 mg/kg | NT |
|  |  |  | 0% @ 20 mg/kg |  |
| 152 | 0.171 | 1.39 | 0% @ 2 mg/kg | NT |
|  |  |  | 0% @ 20 mg/kg |  |
| 153 | 1.45 | NT | NT | NT |
| 154 | 20.1 | >22.6 | NT | NT |
| 155 | 0.259 | 1.31 | NT | NT |
| 156 | 0.295 | 1.22 | NT | NT |
| 157 | 0.332 | NT | NT | NT |
| 158 | 2.44 | 5.84 | NT | NT |
| 159 | 0.543 | NT | NT | NT |
| 160 | 0.461 | 1.19 | NT | NT |
| 161 | 0.134 | <0.647 | NT | NT |
| 162 | 4.71 | NT | NT | NT |
| 163 | 0.180 | NT | NT | NT |
| 164 | 2.65 | NT | NT | NT |
| 165 | 0.364 | 2.40 | NT | NT |
| 166 | 0.205 | NT | NT | NT |
| 167 | 0.175 | NT | NT | NT |
| 168 | 0.180 | <0.626 | 0% @ 2 mg/kg | NT |
|  |  |  | 0% @ 20 mg/kg |  |
| 169 | 0.661 | >20.7 | NT | NT |
| 170 | 0.910 | >21.7 | NT | NT |
| 171 | 0.927 | NT | NT | NT |
| 172 | NT | 8.10 | NT | 12.5% @ 2 × 2 mg/kg |
|  |  |  |  | 25% @ 2 × 20 mg/kg |
| 173 | NT | 8.40 | NT | 25% @ 2 × 2 mg/kg |
|  |  |  |  | 25% @ 2 × 20 mg/kg |
| 174 | NT | 9.05 | NT | NT |
| 175 | 1.39 | 5.28 | NT | 0% @ 2 × 2 mg/kg |
|  |  |  |  | 25% @ 2 × 20 mg/kg |
| 176 | NT | 5.15 | NT | NT |
| 177 | NT | 5.16 | NT | NT |
| 178 | NT | 9.50 | NT | NT |
| 179 | NT | 5.16 | NT | NT |
| 180 | NT | 9.40 | NT | NT |
| 181 | NT | 11.4 | NT | NT |

TABLE 4-continued

In vitro and in vivo antibacterial activity of compounds of Formulas I, II and III.

| Cmpd. No. | IC$_{50}$ ($\mu$M) | MIC ($\mu$g/mL) | In Vivo, single dose (% of mice rescued) | In Vivo, double dose (% of mice rescued) |
|---|---|---|---|---|
| 182 | 2.85 | 5.18 | NT | NT |
| 183 | 6.38 | 10.8 | NT | NT |

[a]NT = not tested

While this invention has been particularly shown and described with references to preferred embodiments thereof, it will be understood by those skilled in the art that various changes in form and details can be made therein without departing from the scope of the invention encompassed by the appended claims.

What is claimed is:

1. A compound of the formula

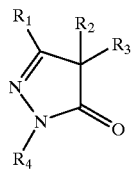

wherein
  $R_1$ is substituted aryl, or substituted or unsubstituted heteroaryl;
  $R_2$ and $R_3$ are each, independently, hydrogen; substituted or unsubstituted, linear, cyclic or branched alkyl; substituted or unsubstituted aminoalkyl; substituted or unsubstituted arylalkyl; substituted or unsubstituted heteroarylalkyl; or substituted or unsubstituted heteroarylcarbonyl; and
  $R_4$ is a substituted or unsubstituted phenyl group, wherein the aryl group represented by $R_1$ is substituted with one or more substitutents selected from methylenedioxo, aryl or heterocyclic; and the heteroaryl group represented by $R_1$ is selected from pyrimidyl, quinolyl, isoquinolyl, pyrrolyl, quinoxalyl, imidazolyl, oxazolyl, isoxazolyl, pyrazolyl, pyrazolyl, thiadiazolyl, oxadiazolyl, indazolyl, thiazolyl, isothiazolyl, tetrazolyl, benzo(b)thienyl, benzimidazolyl, benzoxazolyl, benzothiazolyl, benzothiadiazolyl, benzoxadiazolyl, indolyl, tetrahydroindolyl, azaindolyl, indazolyl, quinolinyl, imidazopyridyl, puryl, pyrrolo[2,3-d]pyrimidyl, pyrazolo[3,4-d]pyrimidyl).

2. The compound of claim 1 wherein $R_4$ is a phenyl group substituted by one or more substituents independently selected from the group consisting of halogen, nitro, cyano and trifluoromethyl.

3. The compound of claim 2 wherein $R_4$ is 3,5-dichlorophenyl or 3,5-bis(trifluoromethyl)phenyl.

4. The compound of claim 1 wherein $R_1$ is selected from the group consisting of 4-(1-morpholinyl)phenyl, 4-(4-carboxy-1-piperazinyl)phenyl and 2-pyridylcarbonyl.

5. The compound of claim 1 wherein $R_2$ and $R_3$ are each independently selected from the group consisting of hydrogen, dimethylaminomethyl, methyl, ethyl, 2-propyl, 1-pyrrolidinyl-$C_1$–$C_4$-alkyl; pyridyl-$C_1$–$C_4$-alkyl; 3-carboxyphenylmethyl, 4-carboxyphenylmethyl, 3-(1-morpholinylcarbonyl)phenylmethyl.

6. The compound of claim 5 wherein $R_3$ is hydrogen or methyl.

7. A compound of the formula:

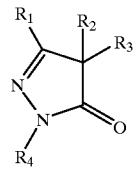

wherein
  $R_1$ and $R_2$ together are —$(CH_2)_n$—, wherein n is 3 or 4;
  $R_3$ is a substituted or unsubstituted aminoalkyl; substituted or unsubstituted arylalkyl; substituted or unsubstituted heteroarylalkyl; or substituted or unsubstituted heteroarylcarbonyl; and
  $R_4$ is a substituted or unsubstituted phenyl group.

8. A compound of the formula

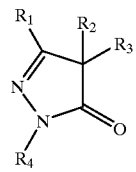

wherein
  $R_1$ is substituted or unsubstituted aryl, substituted or unsubstituted arylalkyl, substituted or unsubstituted alkyl, perfluoroalkyl, heteroaryl, carboxy, substituted or unsubstituted carboxamido, substituted or unsubstituted amino or alkoxycarbonyl;
  $R_2$ and $R_3$ together form =N—OH or a substituted or unsubstituted alkylidene group selected from 4-methoxyphenyl-CH=; 2-,3- or 4-pyridyl-CH=; isopropylidene; 2-,3- or 4-carboxyphenyl-CH=; methycarbonyl-CH=; phenylcarbonyl-CH=; 4-(N,N-diethylamino)phenyl-CH=; 4-(3-(N,N-dimethylamino)propoxy)phenyl-CH=; 2-,3- or 4-pyridyl-CH=; 1-methyl-4-piperidinyl-CH=; N-methyl-2-pyrrolyl-CH=; 2- or 3-thienyl-CH=; 2- or 3-furanyl-CH=; 2-thiazolyl; 4-thiomethoxyphenyl-CH=; 4-thiopyranyl-CH=; 1-(N-ethoxycarbonyl)-4-piperidinyl-CH=; 3-(2-oxo)indolyl-CH=; 2-,3- or 4-methoxycarbonylphenyl-CH=; 2-hydroxymethylfuranyl-CH=; (HO$_2$C)CH=; (HO$_2$C)$_2$CH=; HO$_2$CCH$_2$CH=; 3-(2-oxo indolinyl)-CH=; 3-(4-methylpiperidinylcarbonyl)phenyl-CH=; 3-(morpholyl-4-carbonyl)phenyl-CH= and 3-(N-(2-hydroxyethyl)aminocarbonylphenylCH=; and
  $R_4$ is a substituted or unsubstituted phenyl group.

9. A compound represented by the following structural formula:

10. A method of treating a microbial infection in a patient, comprising administering to the patient a therapeutically effective amount of a compound of the formula:

wherein
- $R_1$ is substituted or unsubstituted aryl, substituted or unsubstituted arylalkyl, substituted or unsubstituted alkyl, perfluoroalkyl, heteroaryl, carboxy, substituted or unsubstituted carboxamido, substituted or unsubstituted amino or alkoxycarbonyl; $R_2$ and $R_3$ are each, independently, hydrogen; substituted or unsubstituted, linear, cyclic or branched alkyl; substituted or unsubstituted aminoalkyl; substituted or unsubstituted arylalkyl; substituted or unsubstituted heteroarylalkyl; or substituted or unsubstituted heteroarylcarbonyl; or
- $R_2$ and $R_3$ together form =N—OH or a substituted or unsubstituted alkylidene group; or
- $R_1$ and $R_2$ together are —$(CH_2)_n$—, wherein n is 3 or 4; and
- $R_4$ is a substituted or unsubstituted phenyl group.

11. The method of claim 10 wherein $R_4$ of the compound is a phenyl group substituted by one or more substituents independently selected from the group consisting of halogen, nitro, cyano and trifluoromethyl.

12. The method of claim 11 wherein $R_4$ of the compound is 3,5-dichlorophenyl or 3,5-bis(trifuoromethyl)phenyl.

13. The method of claim 10 wherein $R_1$ of the compound is substituted or unsubstituted phenyl; substituted or unsubstituted benzyl; linear or branched $C_1$–$C_6$-alkyl; trifluoromethyl; or substituted or unsubstituted pyridyl.

14. The method of claim 13 wherein $R_1$ of the compound is selected from the group consisting of phenyl, 4-methylphenyl, 2-methylphenyl, 3-methylphenyl, 4-fluorophenyl, 3-fluorophenyl, 2-fluorophenyl, methyl, trifluoromethyl, ethyl, n-propyl, 2-propyl, n-pentyl, 2-pentyl, 3-pentyl, 4-(1-morpholinyl)phenyl, 4-(4-carboxy-1-piperazinyl)phenyl; 2-pyridylcarbonyl; amino, carboxy and benzyl.

15. The method of claim 10 wherein $R_1$ and $R_2$ of the compound together form —$(CH_2)_3$— or —$(CH_2)_4$—.

16. The method of claim 10 wherein $R_2$ and $R_3$ of the compound together form =N—OH or a substituted or unsubstituted alkylidene group.

17. The method of claim 10 wherein $R_2$ and $R_3$ of the compound are each independently selected from the group consisting of hydrogen, dimethylaminomethyl, methyl, ethyl, 2-propyl, 1-pyrrolidinyl-$C_1$–$C_4$-alkyl; pyridyl-$C_1$–$C_4$-alkyl; 3-carboxyphenylmethyl, 4-carboxyphenylmethyl, 3-(1-morpholinylcarbonyl)phenylmethyl.

18. The method of claim 17 wherein $R_3$ of the compound is hydrogen or methyl.

19. The method of claim 10 wherein $R_2$ and $R_3$ of the compound together are substituted or unsubstituted linear or branched $C_1$–$C_6$-alkylidene group.

20. The method of claim 19 wherein $R_2$ and $R_3$ of the compound together are 4-methoxyphenyl-CH=; dimethylamino-CH=; 2-,3- or 4-pyridyl-CH=; isopropylidene; 2-,3- or 4-carboxyphenyl-CH=; methycarbonyl-CH=; phenylcarbonyl-CH=; 4-(N,N-diethylamino)phenyl-CH=; 4-(3-(N,N-dimethylamino)propoxy)phenyl-CH=; 2-,3- or 4-pyridyl-CH=; 1-methyl-4-piperidinyl-CH=; N-methyl-2-pyrrolyl-CH=; 2- or 3-thienyl-CH=; 2- or 3-furanyl-CH=; 2-thiazolyl; 4-thiomethoxyphenyl-CH=; 2- or 3-indolyl CH=; 4-thiopyranyl-CH=; 1-(N-ethoxycarbonyl)-4-piperidinyl-CH=; 3-(2-oxo)indolyl-CH=; N-methyl-3-indolyl-CH=; 2-,3- or 4-methoxycarbonylphenyl-CH=; 2-hydroxymethylfuranyl-CH=; ($HO_2C$)CH=; ($HO_2C$)$_2$CH=; $HO_2CCH_2$CH=; 3-(2-oxo indolinyl)-CH=; 3-(4-methylpiperidinylcarbonyl)phenyl-CH=; 3-(morpholyl-4-carbonyl)phenyl-CH= or 3-(N-(2-hydroxyethyl)aminocarbonylphenylCH=.

21. A compound of the formula wherein
- $R_1$ is substituted or unsubstituted aryl, substituted or unsubstituted arylalkyl, substituted or unsubstituted alkyl, perfluoroalkyl, heteroaryl, carboxy, substituted or unsubstituted carboxamido, substituted or unsubstituted amino or alkoxycarbonyl;
- $R_2$ is substituted or unsubstituted heteroarylcarbonyl;
- $R_3$ is hydrogen; substituted or unsubstituted, linear, cyclic or branched alkyl; substituted or unsubstituted aminoalkyl; substituted or unsubstituted arylaLkyl; substituted or unsubstituted heteroarylalkyl; or substituted or unsubstituted heteroarylcarbonyl; and
- $R_4$ is a substituted or unsubstituted phenyl group.

22. The method of claim 10 wherein the microbial infection is a bacterial infection.

23. The method of claim 10 wherein the bacterial infection is an infection by *S. aureus* or *S. pneumoniae*.

* * * * *